United States Patent
Xin et al.

(10) Patent No.: US 10,253,326 B2
(45) Date of Patent: Apr. 9, 2019

(54) MUTANT SORGHUM BICOLOR HAVING ENHANCED SEED YIELD

(71) Applicants: The United States of America, as represented by the Secretary of Agriculture, Washington, DC (US); Cold Spring Harbor Laboratory, Cold Spring Harbor, NY (US)

(72) Inventors: Zhanguo Xin, Lubbock, TX (US); Gloria B. Burow, Lubbock, TX (US); Chad M Hayes, Lubbock, TX (US); John J. Burke, Lubbock, TX (US); Doreen Ware, Melville, NY (US); Yinping Jiao, Cold Spring Harbor, NY (US)

(73) Assignees: The United States of America, as represented by the Secretary of Agriculture, Washington, DC (US); Cold Spring Harbor Laboratory, Cold Spring Harbor, NY (US)

( * ) Notice: Subject to any disclaimer, the term of this patent is extended or adjusted under 35 U.S.C. 154(b) by 130 days.

(21) Appl. No.: 15/086,992

(22) Filed: Mar. 31, 2016

(65) Prior Publication Data
US 2016/0289696 A1    Oct. 6, 2016

Related U.S. Application Data

(60) Provisional application No. 62/142,669, filed on Apr. 3, 2015.

(51) Int. Cl.
| | | |
|---|---|---|
| C12N 15/82 | (2006.01) | |
| C12N 9/02 | (2006.01) | |
| C12Q 1/6895 | (2018.01) | |

(52) U.S. Cl.
CPC ....... *C12N 15/8261* (2013.01); *C12N 9/0069* (2013.01); *C12N 15/827* (2013.01); *C12N 15/8247* (2013.01); *C12Q 1/6895* (2013.01); *C12Q 2600/13* (2013.01); *C12Q 2600/156* (2013.01); *C12Y 113/11012* (2013.01)

(58) Field of Classification Search
CPC .................................................. C12N 15/8261
USPC ....................................................... 800/276
See application file for complete search history.

(56) References Cited

U.S. PATENT DOCUMENTS

| | | | |
|---|---|---|---|
| 9,258,998 B2* | 2/2016 | Dellaporta | A01N 37/42 |
| 2014/0068798 A1 | 3/2014 | Xin et al. | |
| 2016/0264986 A1 | 9/2016 | Xin et al. | |

OTHER PUBLICATIONS

Advanta US, Inc. and USDA/ARS Material Transfer Agreement, signed Mar. 2, 2015 and Feb. 18, 2015.
Amsterdam, Adam et al., "Mutagenesis strategies in zebrafish for identifying genes involved in development and disease", (2006), Trends in Genetics 22(9):473-478.
Acosta, Ivan F. et al., "tasselseed1 Is a Lipoxygenase Affecting Jasmonic Acid Signaling in Sex Determination of Maize", (2009), Science, 323:262-265.
Ashikari, Motoyuki et al., "Cytokinin Oxidase Regulates Rice Grain Production", (2005) Science 309:741-745.
Bentley, Alyssa et al., "Targeted Recovery of Mutations in *Drosophila*", (2000), Genetics 156:1169-1173.
Brown, P. J. et al., "Inheritance of inflorescence architecture in sorghum", (2006), Theoretical and Applied Genetics 113:931-942.
Burow, Gloria et al., "Characterization of a Multiseeded (msd1) Mutant of Sorghum for Increasing Grain Yield", (2014), Crop Science 54:1-8.
Burow, Gloria et al., "Multi-Seeded sorghum mutants as a novel trait to boost grain yield (abstract)", First International Conference on Genomics, Traits, and Business,Charlotte, NC, (Sep. 2014), P1:04.
Burow, Gloria et al., "Analysis of Cold Tolerance and "multiseeded" Genetic Stocks of Sorghum", Proceeding of the 2013 SICNA Meeting, (2013) PowerPoint Presentation, 23 slides.
Burow, Gloria et al., "Mutant Resources in Sorghum: Focus on Novel Multiseeded Class", Translational Cereal Genomics Meeting, Vienna, Austria, (2014) PowerPoint Presentation, 16 slides.
Casady, A.J. et al., "Effect of the Twin-seeded Character on Sorghum Performance", (1977) Crop Science 17:117-120.
Chuck, George et al., "The maize tasselseed4 microRNA controls sex determination and meristem cell fate by targeting Tasselseed6/indeterminate spikelet1", (2007), Nature Genetics—Letters, pp. 1-5, published online Nov. 18, 2007; doi:10.1038/ng.2007.20.
Duggan, B. L. et al., "Yield component variation in winter wheat grown under drought stress", Canadian Journal of Plant Science, (2000) p. 739-745.
Ejeta, Gebisa and John Axtell, "Mutant gene in sorghum causing leaf "reddening" and increased protein concentration in the grain", Journal of Heredity, (1985) 76:301-302.
Henikoff, Steven et al., "Tilling. Traditional Mutagenesis Meets Functional Genomics", (2004) Plant Physiology 135:630-636.
Maccarrone, M. et al., "Lipoxygenases and their involvement in programmed cell death", (2001), Cell Death and Differentiation 8:776-784.
Ksu, Agricultural Research Center and USDA/ARS Material Transfer Agreement, signed Oct. 18, 2012.

(Continued)

*Primary Examiner* — Li Zheng
(74) *Attorney, Agent, or Firm* — John D. Fado; David L. Marks; Gail E. Poulos

(57) ABSTRACT

Genetically altered sorghum plants expressing the multi-seeded #2 phenotype contain one of two genomic alterations in the Sb06g018040 gene which result in reduced activity of the encoded protein, a class II 13-lipoxygenase. This phenotype and genotype are referred to as msd2. These alterations result in increased number of seeds and seed weight, thus increasing the yield of the genetically altered plant. These alterations can be generated in the ortholog genes in maize (TS1), rice, barley, and other monocot plants, generating the MSD2 phenotype. The seeds of one particular MSD2 *Sorghum bicolor* has been deposited with ATCC and assigned Accession Number PTA-121634.

15 Claims, 4 Drawing Sheets

Specification includes a Sequence Listing.

(56) References Cited

OTHER PUBLICATIONS

Monsanto and USDA/ARS Material Transfer Agreement, signed Jan. 13, 2014.
Nidera USA and USDA/ARS Material Transfer Agreement, signed Oct. 16, 2014 and Nov. 2014.
Oria, Maria P. et al., "A highly digestible sorghum mutant cultivar exhibits a unique folded structure of endosperm protein bodies", (2000) PNAS 97(10):5065-5070.
Paterson, Andrew H. "Genomics of Sorghum", (2008) International Journal of Plant Genomics vol. 2008, Article ID 362451, 6 pages.
Paterson, Andrew H. et al., "The Sorghum bicolor genome and the diversification of grasses", (2009) Nature 457:551-556.
Reynolds, Matthew et al., "Raising yield potential in wheat", (2009) Journal of Experimental Botany 60(7):1899-1918.
Richards, R.A., "Selectable traits to increase crop photosynthesis and yield of grain crops", (2000) Journal of Experimental Botany 51:447-458.
Saballos, Ann, "Development and Utilization of Sorghum as a Bioenergy Crop", Editor W. Vermerris, Genetic Improvement of Bioenergy Crops, Chapter 8, pp. 211-248.
Saeed, Mohammad et al., "Yield Component Analysis in Grain Sorghum", (1986) Crop Science 26:346-351.
Scott Seed Company and USDA/ARD Material Transfer Agreement, signed Sep. 2012.
Xin, Zhanguo et al., "Applying genotyping (Tilling) and phenotyping analyses to elucidate gene function in a chemically induced sorghum mutant population", (2008), BMC Plant Biology 8:103 14 pgs.
Xin, Zhanguo et al., "An Induced Sorghum Mutant Population Suitable for Bioenergy Research", (2009), Bioenergy Res. 2:10-16.
Xin, Zhanguo et al., "A high throughput DNA extraction method with high yield and quality", (2012) Plant Methods 8:26 7 pgs.
Xin, Zhanguo et al., "Multi—seeded Sorghum Mutants as a Novel Trait to Boost Grain Yield" Poster.
Xin, Zhanguo et al., "SNP-tagged Mutant Library in Sorghum" Poster submission and Abstract for The 2nd Plant Genomics Congress: Asia, Mar. 2015.
Xin, Zhanguo et al., "SNP-tagged Mutant Library in Sorghum" Slide Presentation for The 2nd Plant Genomics Congress: Asia, Mar. 2015, 31 slides.
Xin, Zhanguo et al., "Potential of Multiseeded Mutant (msd) to Boost Sorghum Grain Yield", Abstract, Jan. 11, 2015.
Xin, Zhanguo et al., "Potential of Multiseeded Mutant (msd) to Boost Sorghum Grain Yield", Slide Presentation, 29 slides.
Chromatin, Inc and USDA/ARS Material Transfer Agreement, signed Oct. 25, 2012.
Chromatin, Inc and USDA/ARS Material Transfer Agreement, signed Dec. 16, 2014.
Fuessner, I. et al., "The Lipoxygenase Pathway", (2002) Annual Reviews Plant Biology 53:275-297.
Keygene N.V. and USDA/ARS Material Transfer Agreement, signed Oct. 29, 2014.
Nextsteppe, Inc and USDA/ARS Material Transfer Agreement, signed Jan. 23, 2012.
Nuseed Americas, Inc and USDA/ARS Material Transfer Agreement, signed Sep. 28, 2012.
Pioneer Hi-Bred International, Inc and USDA/ARS Material Transfer Agreement, signed Aug. 24, 2011.
Xin, Z. et al., "Multi-Seeded Sorghum Mutants As a Genetic Resource for Enhancing Sorghum Yield", Presented at ASA Annual Conference, Nov. 3, 2014, Abstract.
Burow, G. et al., "Characterization of a multi seeded (msd) mutant of sorghum exhibiting significant enhancement of seed number", Translational Cereal Genomics Meeting, Vienna, Austria, (2014), Abstract.

\* cited by examiner

MUTANT SORGHUM BICOLOR HAVING ENHANCED SEED YIELD

BACKGROUND OF INVENTION

Field of Invention

This invention relates to a novel mutation in a sorghum gene which increases the seed yield in sorghum. The amino acid sequence of this mutated gene and its encoded protein are included. This invention also relates to genetically altered plants having this mutated gene and/or containing the mutated protein and which have increased flower production and seed yield.

Description of the Prior Art

Grain yield is determined by the number of plants per acre, seed number per plant (also called "seed yield"), and seed weight. Among all these yield components, seed number per plant is a major determinant of grain yield in sorghum [*Sorghum bicolor* (L.) Moech] and other cereal crops (Saeed, et al., *Crop Sci.* 26:346-351 (1986); Duggan, et al., *Can. J. Plant Sci.* 80:739-745 (2000); Richards, *J. Exp. Bot.* 51:447-458 (2000); Ashikari, et al., *Science* 309: 741-745 (2005); Reynolds, et al., *J. Exp. Bot.* 60:1899-1918 (2009)). Increased seed number and seed size, which are directly related to improved grain yield, were common goals during domestication of cereal crops resulting in inadvertent selection of genetic stocks with greater seed number and larger seeds (Zohary, et al., *Domestication of Plants in the Old World: The Origin and Spread of Cultivated Plants in West Asia. Europe, and the Mediterranean Basin.* 4 ed. Oxford University Press, Oxford, U.K. (2012)).

Seed number per panicle is determined by several attributes of the inflorescence, including the number and length of the primary and secondary flower branches, and fertility of spikelets. In sorghum, the inflorescence or panicle has a main rachis on which many primary branches are developed. Secondary branches and sometimes tertiary branches develop from the secondary branches (Brown, et al., *Theor. Appl. Genet.* 113:931-942 (2006); Burow, et al., *Crop Sci.* 54:2030-2037 (2014)). The main inflorescence, primary branches, secondary branches, and tertiary branches all end with a terminal triplet of spikelets, which consist of one sessile bisexual spikelet and two lateral staminate pedicellate spikelets (Walters and Keil, *Vascular Plant Taxonomy.* 4th ed. Kendall/Hunt Pub. Co., Dubuque, Iowa, USA (1988)). Below the terminal spikelets, one or more spikelet pair can develop, and these adjacent spikelet pairs consist of one sessile and one pedicellate spikelet. In the wild-type sorghum line BTx623 and all other characterized natural sorghum accessions, only the sessile spikelets are perfect flowers and can develop into seeds. The development of pedicellate spikelets is arrested at various stages in different sorghum lines. In some lines, the pedicellate spikelets can develop anthers and shed viable pollen, but few lines can develop ovary and produce viable seeds (Karper and Stephens, *J. Hered.* 27:183-194 (1936)). Thus, the pedicellate spikelets in the wild type eventually abort.

Recently, a novel group of sorghum mutants were generated by subjecting sorghum seeds to ethyl methane sulfonate (EMS). The seeds were grown and back-crossed with wild-type sorghum line BTx623 and the seeds from those crosses were germinated. Many of the mutated sorghum plants were isolated and characterized. These sorghum mutants were designated as multiseeded (msd) mutants because the developmental arrest of the pedicellate spikelets was released (Burow, et al. (2014)). See also U.S. Patent App. Publication No. 2014-0068798. While all of these mutated sorghum mutants had increased seed count, they exhibited different and distinctive phenotypes. Only recently has one genetic mutation which results in one of the distinctive phenotypes been characterized. This msd1 gene and its distinctive phenotype is the subject matter of U.S. Patent App. 62/132,574 filed on Mar. 13, 2015. Through next-generation sequencing of the pooled genomic DNA of homozygous mutants selected from a backcrossed F2 population derived from a cross of msd1-1 (p12) to BTx623, the MSD1 gene has been identified as a TCP-domain plant-specific transcription factor.

The genetic mutations in another set of sorghum plants with an interesting MSD phenotype are investigated, and the mutations that give rise to the identified phenotype are described herein, along with a description of the phenotype.

BRIEF DESCRIPTION OF THE INVENTION

It is an object of this invention to have a genetically altered plant or parts thereof and its progeny having the multiseeded phenotype (msd), and in particular, the MSD2 phenotype. It is a further object of this invention that the plant or parts thereof have a mutation in a gene that encodes a class II 13-lipoxygenase gene having an amino acid sequence that is at least 80% identical to SEQ ID NO: 2 such that the mutation in the class II 13-lipoxygenase gene causes a reduction in the activity of the mutated class II 13-lipoxygenase compared to the non-genetically altered class II 13-lipoxygenase and such that the reduced activity of the mutated class II 13-lipoxygenase causes the MSD2 phenotype. It is another object of this invention that the genetically altered plant or parts thereof and its progeny have reduced amount of 8-cis-jasmonic acid in its panicle tissue compared to the amount of 8-cis-jasmonic acid in a non-genetically altered plant. It is further object of this invention to have a cell, tissue culture of cells, seed, fruit, pollen, and flower from the genetically altered plant or its progeny described herein. The genetically altered plant can be sorghum, maize, rice, barley, oats, wheat, rye, millet, and triticale.

It is an object of this invention to have a genetically altered sorghum or parts thereof and its progeny having the MSD2 phenotype. It is a further object of this invention that the genetically altered sorghum or parts thereof and its progeny have a genetic alteration in the Sb06g018040 gene (SEQ ID NO: 1) which encodes a class II 13-lipoxygenase (SEQ ID NO: 2) such that the genetically altered class II 13-lipoxygenase has reduced activity or no activity compared to the non-genetically altered class II 13-lipoxygenase or that no class II 13-lipoxygenase protein is produced. In one embodiment, the genetically altered Sb06g018040 gene has a C→T mutation at either nucleotide 1880 (msd2-1; p19; SEQ ID NO: 4 (genomic sequence); SEQ ID NO: 6 (coding sequence)) or nucleotide 2037 in SEQ ID NO: 1 (msd2-2; p8; SEQ ID NO: 7 (genomic sequence); SEQ ID NO: 9 (coding sequence)). It is further object of this invention that the genetically altered Sb06g018040 gene has the DNA sequence of SEQ ID NO: 4 or SEQ ID NO: 7. It is another object of this invention that the genetically altered Sb06g018040 gene has a coding sequence of SEQ ID NO: 6 or SEQ ID NO: 9. It is another object of this invention that the genetically altered Sb06g018040 gene generates a protein having the amino acid sequence of SEQ ID NO: 5 (msd2-1; p19) or SEQ ID NO: 8 (msd2-2; p8). Another object of this invention is that the genetically altered Sb06g018040 gene has a mutation that destroys a splice site sequence which causes a null mutation, such as a G→A mutation at nucleotide 2214 of SEQ ID NO: 1, the mutated sequence is provided in SEQ ID NO: 17 (msd2-4; p30). It is another object of this invention that the genetically altered sorghum or parts thereof and its progeny have reduced amount of 8-cis-jasmonic acid in its panicle tissue compared to the amount of 8-cis-jasmonic acid in a non-genetically altered plant. It is further object of this invention to have a cell, tissue culture of cells, seed, fruit, pollen, and flower from the genetically altered sorghum or its progeny described herein. It is another object of this invention that the genetically altered sorghum or its progeny have ATCC Accession Number PTA-121634.

It is another object of this invention to have a genetically altered plant or parts thereof and its progeny having the MSD2 phenotype as a result of a C→T mutation in a class II 13-lipoxygenase gene that encodes a protein that is at least 80% identical to Sb06g018040 (SEQ ID NO: 2). Such C→T mutation occurs at the Sb06g018040 ortholog gene's DNA sequence that is equivalent to nucleotide 1880 or 2037 in SEQ ID NO: 1. This C→T mutation results in reduced or no class II 13-lipoxygenase activity compared to wild-type or non-genetically altered class II 13-lipoxygenase activity. In one embodiment, the C→T mutation at the equivalent position in each plant's Sb06g018040 ortholog to nucleotide 1880 in SEQ ID NO: 1 causes a translation termination instead of glutamine amino acid at the equivalent to amino acid number 402 of Sb06g018040 (see SEQ ID NO: 5). In another embodiment, the C→T mutation at the equivalent position in each plant's Sb06g018040 ortholog to nucleotide 2037 in SEQ ID NO: 1 causes a valine amino acid instead of an alanine amino acid at the equivalent to amino acid number 423 of Sb06g018040 (see SEQ ID NO: 8). It is another object of this invention that the genetically altered plant has a mutation that destroys a splice site sequence which causes a null mutation; such as a G→A mutation at nucleotide 2214 of SEQ ID NO: 1, the mutated sequence is provided in SEQ ID NO: 17 (msd2-4; p30). The genetically altered plant or parts thereof and its progeny have reduced amount of 8-cis-jasmonic acid in its panicle tissue compared to the amount of 8-cis-jasmonic acid in a non-genetically altered plant. This reduced activity of the genetically altered class II 13-lipoxygenase and/or reduced levels of 8-cis-jasmonic acid in panicle tissue correlates with the MSD2 phenotype. It is another object of the invention that the genetically altered plant or parts thereof and its progeny can be a monocotyledon. It is a further object of the invention that the genetically altered plant or parts thereof and its progeny can be a cereal crop plant or a grass. It is further object of this invention to have a cell, tissue culture of cells, seed, fruit, pollen, and flower from the genetically altered plant or its progeny described herein.

It is an object of this invention to have a genetically altered sorghum that has an altered class II 13-lipoxygenase protein with reduced activity compared to non-genetically altered class II 13-lipoxygenase protein such that the genetically altered sorghum expresses the MSD2 phenotype. It is a further object of this invention that the altered class II 13-lipoxygenase protein is encoded by a polynucleotide which has a coding sequence of SEQ ID NO: 6, SEQ ID NO: 9, a sequence that is at least 95% identical to the coding sequence of SEQ ID NO: 6, a sequence that is at least 95% identical to the coding sequence of SEQ ID NO: 9, or a polynucleotide having the sequence of SEQ ID NO: 17.

It is an object of this invention to have a genetically altered plant or parts thereof and its progeny that has the MSD2 phenotype, the genetically altered plant or parts thereof and its progeny containing a genetic alteration in a class II 13-lipoxygenase gene such that the genetically altered plant or parts thereof and its progeny have a reduced amount of 8-cis-jasmonic acid in its panicle tissue compared to the amount of 8-cis-jasmonic acid in a non-genetically altered plant. This reduced amount of 8-cis-jasmonic acid in panicle tissue correlates with MSD2 phenotype. It is another object of this invention that the genetically altered plant or parts thereof and its progeny are a monocot plant, and, more specifically, cereal crops and grasses. The cereal crops can be sorghum, maize, rice, barley, oats, wheat, rye, millet, and triticale. It is a further object of this invention to have a cell, tissue culture of cells, seed, pollen, fruit, and flower of this genetically altered plant or its progeny.

It is an object of this invention to have a method for constructing a genetically altered cereal crop or grass plant that has the MSD2 phenotype having the steps of introducing an altered msd2 nucleic acid into a cereal crop or grass plant to provide a genetically altered cereal crop or grass plant and selecting the genetically altered cereal crop or grass plant that is homozygous for the altered msd2 nucleic acid, thereby constructing the genetically altered cereal crop or grass plant and that the genetically altered cereal crop or grass plant has the AMSD2 phenotype. It is a further object of this invention that the cereal crop plant can be sorghum, maize, rice, barley, oats, wheat, rye, millet, or triticale. It is another object of this invention that the step of introducing the altered msd2 nucleic acid occurs via introgression, genomic editing, or exposing the cereal crop or grass plant to a mutagen. It is yet a further object of this invention that the step of selecting the genetically altered cereal crop or grass plant occurs via marker assisted selection. In yet another object of this invention, the altered msd2 nucleic acid contains a mutation in a class II 13-lipoxygenase gene such that the genetically altered cereal crop or grass plant has reduced amount of 8-cis-jasmonic acid in its panicle tissue compared to the amount of 8-cis-jasmonic acid in a non-genetically altered cereal crop or grass plant and that the reduced amount of 8-cis-jasmonic acid in panicle tissue correlates with the MSD2 phenotype.

It is another object of this invention to have a kit, and methods for using a kit, for determining if a plant expresses the MSD2 phenotype caused by a mutated class II 13-lipoxygenase gene. It is another object of this invention that the kit contains at least one pair of polynucleotides; optionally an identifying dye which helps in identify the SNP; optionally a polymerase; and optionally instructions for using of the at least one pair of polynucleotides. In one embodiment of this invention, one pair of the polynucleotides have the sequence of SEQ ID NO: 13 and SEQ ID NO: 14. In another embodiment of this invention, the other pair of polynucleotides have the sequence of SEQ ID NO: 15 and SEQ ID NO: 16. It is a further object of this invention that if the plant possesses the polynucleotide sequence of SEQ ID NO: 13 or SEQ ID NO: 15, then the plant contains the mutated class II 13-lipoxygenase gene and expresses the MSD2 phenotype. In another embodiment of this invention, the kit can contain a set of three polynucleotide primers to distinguish between a genetically altered plant containing one SNP and a wild-type plant; these sets of polynucleotide primers have the sequences as follows: for msd2-1 (p19) SEQ ID NO: 19 (wild-type), SEQ ID NO: 20 (p19), and SEQ ID NO: 21 (common); for msd2-2 (p8) SEQ ID NO: 22 (wild-type), SEQ ID NO: 23 (p8), and SEQ ID NO: 24 (common); and for msd2-4 (p30) SEQ ID NO: 25 (wild-type), SEQ ID NO: 26 (p30), and SEQ ID NO: 27 (common).

Figure 1:
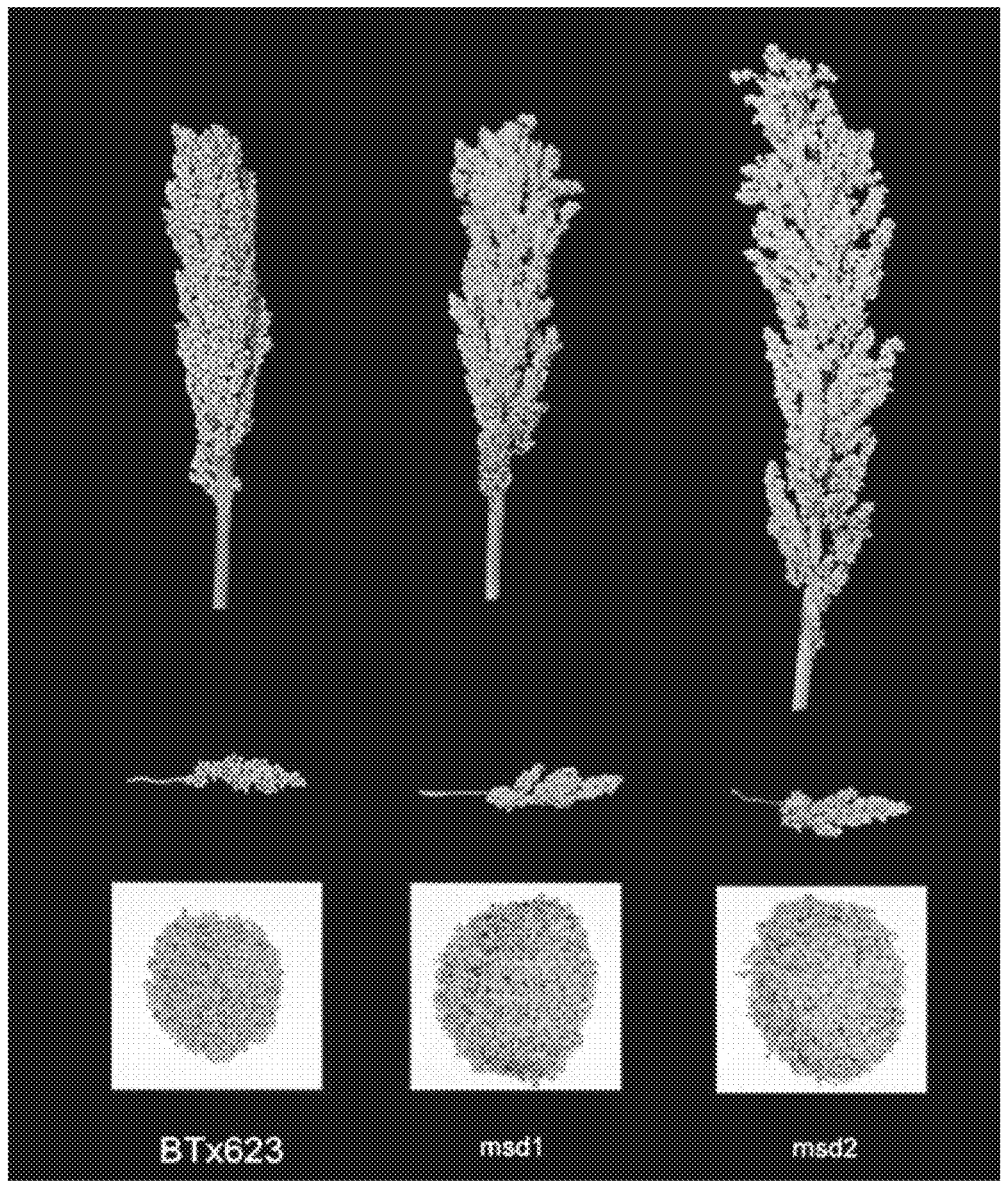
FIG. 1 shows the phenotypic differences between BTx623 wild-type sorghum yield (left), msd1 sorghum yield (middle), and msd2 sorghum yield (right).

STATEMENT REGARDING DEPOSIT OF BIOLOGICAL MATERIAL UNDER THE TERMS OF THE BUDAPEST TREATY

On or before Sep. 30, 2014, the inventors deposited 2,500 seed of *Sorghum bicolor* strain msd2-1 (p19), as described herein, with American Type Culture Collection (ATCC) located at 10801 University Blvd., Manassas, Va. 20110, in a manner affording permanence of the deposit and ready accessibility thereto by the public if a patent is granted. The deposit has been made under the terms of the Budapest Treaty on the International Recognition of the Deposit of Microorganisms for the Purposes of Patent Procedure and the regulations thereunder. The deposit's accession number is ATCC Accession Number PTA-121634.

All restrictions on the availability to the public of *Sorghum bicolor* strain msd2-1 (p19) which has been deposited as described herein will be irrevocably removed upon the granting of a patent covering this particular biological material.

The *Sorghum bicolor* strain msd2-1 (p19) has been deposited under conditions such that access to the organism is available during the pendency of the patent application to one determined by the Commissioner to be entitled thereto under 37 C.F.R. § 1.14 and 35 U.S.C § 122.

The deposited biological material will be maintained with all the care necessary to keep it viable and uncontaminated for a period of at least five years after the most recent request for the furnishing of a sample of the deposited microorganism, and in any case, for a period of at least thirty (30) years after the date of deposit for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION OF THE INVENTION

Four genetically altered sorghum plants examined herein have a "multi-seeded" mutation #2 (MSD2) with a distinctive phenotype and genetic alteration that differs from the previously identified genetically altered MSD1 sorghum. The four genetically altered sorghum plants described herein have at least one mutation in a gene referred to herein as MSD2. The equivalent gene in sorghum strain BTx623 is identified as Sb06g018040 (the wild-type gene). Furthermore, Sb06g018040 and MSD2 are homologs to maize Tassel Seed 1 (TS1), a sex determinant gene that enables the staminate tassel to set seeds (Acosta, et al., *Science* 323: 262-5 (2009)). TS1, Sb06g018040 and MSD2 encode a class II 13-lipoxygenase. As demonstrated below, a change in the amino acid sequence of this class II 13-lipoxygenase results in increased seed yield in the genetically altered sorghum having the MSD2 phenotype. One genetic mutation described herein (identified as both MSD2-1 (p19) and MSD2-3) results in earlier translational termination of the protein resulting in a protein with reduced or no enzymatic activity compared to wild-type (or non-genetically altered) class II 13-lipoxygenase encoded by Sb06g018040. The second genetic mutation (identified as MSD2-2 (p18)) results in the substitution of an alanine with a valine amino acid in this class II 13-lipoxygenase and also results in reduced or no enzymatic activity compared to the wild-type (or non-genetically altered) class II 13-lipoxygenase. The fourth mutation (identified as MSD2-4 (p30)) has a G→A mutation that abolishes a splice site between the third intron and the fourth exon in this class II 13-lipoxygenase gene and also results in reduced or no enzymatic activity compared to the wild-type (or non-genetically altered) class II 13-lipoxygenase. Because MSD2-1 (p19) and MSD2-4 (p30) lack the carboxyl 522 amino acids or the carboxyl 477 amino acids, respectively, of the wild-type class II 13-lipoxygenase, any mutation which results the possible production of a protein having an amino acid of between amino acid 1 and amino acid 447 of SEQ ID NO: 2 will result in the reduced or no class II 13-lipoxygenase activity and thus result in the MSD2 phenotype. Other such mutation can be mutations that destroy other splice site sequences or other mutations which cause an early translational termination of protein (prior to amino acid 447).

This invention involves MSD2 genetic alterations in sorghum and other cereal crops, including but not limited to, corn/maize, rice, barley, oats, wheat, rye, millet, and triticale, which leads to an increase in the number of seeds produced per plant which is an important component to an increase in the plant's grain yield. These MSD2 genetic alterations result in the MSD2 phenotype for which the genetically altered plant has an increased number of flower branches, increased size of flower branches, full fertility of pedicellate spikelets, increased number of flowers, and increased number of seeds (grain). Genetically altered cereal crops having an MSD2 genetic alteration have reduced or no activity of this class II 13-lipoxygenase. Further, the genetically altered cereal crops have highly reduced levels of active class II 13-lipoxygenase or no active class II 13-lipoxygenase in developing panicles compared to the wild-type phenotype. Thus, 8-cis-jasmonic acid production is reduced or completely inhibited in developing panicle in the genetically altered cereal crop plants having the MSD2 phenotype. Not wishing to be bound to any particular hypothesis, this highly-reduced class II 13-lipoxygenase enzymatic activity and reduced amount of 8-cis-jasmonic acid production may result from the genetically altered cereal crop plant expressing one or more other class II 13-lipoxygenase genes, and the enzymes encoded by these other genes could still produce jasmonic acid.

The invention described herein covers any monocot plant (such as cereal crops and grasses) which contains a genetic alteration in a class II 13-lipoxygenase that has high identity, at the amino acid level, to sorghum's Sb06g018040 or maize's TS1 gene; the genetic alteration resulting in a reduced or no activity of the encoded enzyme compared to the wild-type plant's enzymatic activity. The genetic alteration could be a single point mutation in the DNA at the specific nucleotides discussed below, a deletion mutation in the DNA, a null mutation, or another mutation which reduces or inhibits the enzymatic activity of the encoded enzyme. To be clear, some deletion mutations are null mutations. A plant with this MSD2 mutation would have more flower production and more seed production compared to the wild-type plant. The mutation could be a change in the DNA sequence of the gene resulting in (1) early termination of mRNA translation into a protein (one such mutation being C→T at position 1880 in the genomic sequence of the gene (see SEQ ID NO: 1 for wild-type genomic sequence and SEQ ID NO: 4 for mutated genomic sequence)) or at position 1203 in the coding sequence (see SEQ ID NO: 3 for wild-type coding sequence and SEQ ID NO: 6 for mutated coding sequence)) which results in a termination codon or their equivalent nucleotide in the ortholog gene) or (2) the altering of the enzymatic activity of the encoded protein by changing one or more amino acids to one or more different amino acids (one such mutation is C→T mutation at position 2037 in the genomic sequence of the gene (see SEQ ID NO: 1 for wild-type genomic sequence and SEQ ID NO: 7 for mutated genomic sequence)) or at position 1268 in the coding sequence (see SEQ ID NO: 3 for wild-type coding sequence and SEQ ID NO: 9 for mutated coding sequence)) which results in changing an alanine to valine in the encoded protein or their equivalent nucleotide in the ortholog gene) or (3) altering the enzymatic activity of the encoded protein by abolishing a splice site between an exon and an intron or an intron and an exon (one such mutation is G→A mutation at position 2214 in the genomic sequence of the gene; see SEQ ID NO: 1 for wild-type genomic sequence and SEQ ID NO: 17 for the mutated genomic sequence). These types of mutations cause reduced or no enzymatic activity of the encoding protein which results in the observed phenotype. It is also believed that any mutation that causes a loss of at least the carboxyl 477 amino acids of this class II 13-lipoxygenase protein will result in the MSD2 phenotype. Further any null mutation of will result in this MSD2 phenotype.

This invention involves genetically altered sorghum for which the genetic alteration results in a reduction in the amount of jasmonic acid (8-cis jasmonic acid, in one embodiment) in the genetically altered sorghum's panicle tissue compared to the amount of jasmonic acid (8-cis jasmonic acid in one embodiment) in a non-genetically altered sorghum's panicle tissue. The genetically altered sorghum produces an altered MSD2 protein having the amino acid sequence set forth in SEQ ID NO: 5 (msd2-1; p19), SEQ ID NO: 8 (msd2-2; p8), or no MSD2 protein. The altered MSD2 protein is generated from a DNA coding sequence ("coding sequence") set forth in either SEQ ID NO: 6 (msd2-1; p19) or a sequence that is at least 95% identical to SEQ ID NO: 6, or SEQ ID NO: 9 (msd2-2; p8) or a sequence that is at least 95% identical to SEQ ID NO: 9, respectively. Thus, the genetically altered sorghum contains an altered MSD2 gene which generates a coding sequence (SEQ ID NO: 6 (or a sequence that is at least 95% identical to SEQ ID NO: 6) or SEQ ID NO: 9 (or a sequence that is at least 95% identical to SEQ ID NO: 9)) that produces an altered MSD2 protein and genetically altered sorghum expresses the MSD2 phenotype. Also a DNA encoding only amino acids 1 through 402 of SEQ ID NO: 2 or amino acids 1 through 447 of SEQ ID NO: 2 will result in the MSD2 phenotype.

In another embodiment, this invention involves genetically altered plants (monocots in one embodiment; cereal crops in another embodiment; grasses in a third embodiment) that have an altered MSD2 gene which results in a reduction in the amount of jasmonic acid (8-cis jasmonic acid, in one embodiment) in the panicle tissue compared to the amount of jasmonic acid (8-cis jasmonic acid in one embodiment) in panicle tissue in non-genetically altered plants. In one embodiment, the genetically altered plant produces an altered MSD2 protein having the amino acid sequence that is at least 80% identical to the amino acid sequence set forth in either SEQ ID NO: 5 or SEQ ID NO: 8. In this embodiment, the altered MSD2 protein is generated from a coding sequence that encodes this altered MSD2 protein having an amino acid sequence that is at least 800 identical to the amino acid sequence of SEQ ID NO: 5 or SEQ ID NO: 8. In another embodiment, the non-genetically altered plant contains a gene that encodes a class II 13-lipoxygenase that has an amino acid sequence that is at least 800 identical to SEQ ID NO: 2; where in the genetically altered plant, the gene that encodes the class II 13-lipoxygenase is altered such that the altered class II 13-lipoxygenase has reduced or no activity compared to the non-genetically altered class II 13-lipoxygenase, and the genetically altered plant exhibits the MSD2 phenotype. In another embodiment, the non-genetically altered plant contains a gene that encodes a class II 13-lipoxygenase that has reduced or no activity compared to a non-genetically altered class II 13-lipoxygenase because of a missing splice site at an intron or exon, where one such example of a missing splice site that has the sequence of SEQ ID NO: 17.

In another embodiment, any genetically altered plant that contains a null mutation in this class II 13-lipoxygenase gene is included in this invention. For this invention, a null mutation is a DNA alteration that results in no production of the class II 13-lipoxygenase protein, or in production of a protein that lacks class II 13-lipoxygenase activity. Because MSD2-1 (p19) and MSD2-4 (p30) mutations result in a protein having only the first 402 amino acids (MSD2-1) or, possibly the first 447 (MSD2-4) amino acids out of 924 amino acids in the wild-type protein, any mutation that results in a loss of the carboxyl 477 amino acids or more of this class II 13-lipoxygenase protein will result in the MSD2 phenotype and is probably a null mutation.

A mutation to a splice site sequence (a splice site mutation) which causes incorrect splicing of mRNA can be a null mutation. A splice site mutation is a mutation that inserts, deletes or changes a number of nucleotides in the specific site at which splicing takes place during the processing of precursor mRNA into mature mRNA. Splice site consensus sequences that drive exon recognition are located at the very termini of introns. The deletion of the splicing site results in one or more introns remaining in mature mRNA and may lead to the production of abnormal proteins. When a splice site mutation occurs, the mRNA transcript possesses information from these introns that normally should not be included. Introns are supposed to be removed, while the exons are expressed. The mutation must occur at the specific site at which intron splicing occurs: within non-coding sites in a gene, directly next to the location of the exon. The mutation can be an insertion, deletion, frame shift, etc. The splicing process itself is controlled by the given sequences, known as splice-donor and splice-acceptor sequences, which surround each exon. Mutations in these sequences may lead to retention of large segments of intronic DNA by the mRNA, or to entire exons being spliced out of the mRNA. These changes could result in production of a nonfunctional protein. An intron is separated from its exon by means of the splice site. Acceptor-site and donor-site relating to the splice sites signal to the splicesome where the actual cut should be made. These donor sites, or recognition sites, are essential in the processing of mRNA. One example of a splice site mutation is MSD2-4 (p30) in which a G→A mutation at nucleotide 2214 of SEQ ID NO: 1 (see SEQ ID NO: 17 for the sequence containing the altered nucleotide).

Plants, parts of plants, and progeny that "exhibit" or "have" the MSD2 phenotype have the genetic alteration involving a mutation in the gene encoding class II 13-lipoxygenase that has high identity, at the amino acid level, to sorghum's Sb06g018040 or maize's TS1 gene and which have reduced levels or complete inhibition of jasmonic acid production in developing panicle. However, a part of a plant, such as but not limited to, a cell, a protocorm, a pollen, a seed, etc., does not have a panicle. Thus, one is unable to determine if the part of the plant "exhibits" or "has" the MSD2 phenotype simply by looking at the plant's part. However, if the part of the plant has the genetic alteration that is described herein and which can be determined using the molecular biology techniques described herein, then that plant part is considered to "exhibit" or "have" the MSD2 phenotype. A plant that lacks a genetic alteration of the gene encoding the class II 13-lipoxygenase (Sb06g018040, TS1 gene, or an otholog) that does not result in the MSD2 phenotype, and thus the plant does not exhibit the MSD2 phenotype, such a plant is referred to as a "wild-type" or "non-genetically altered" plant, even if the plant has a genetic alteration in the class II 13-lipoxygenase (Sb06g018040, TS1 gene, or an otholog) that does not give rise to the MSD2 phenotype or has a genetic alteration in one or more other genes. Such a wild-type plant is a plant that fails to exhibit the MSD2 phenotype.

It is noted that the MSD2 phenotype is a recessive phenotype. A genetically altered plant needs two copies of the mutated gene to exhibit the MSD2 phenotype. Further, the mutated gene is passed to offspring in a simple Mendelian genetic pattern.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants). It includes plants of a variety of ploidy levels, including aneuploid, polyploid, diploid, haploid and hemizygous. The genetically altered plants described herein can be monocot crops such as sorghum, maize, wheat, rice, barley, oats, rye, millet, and triticale.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology*, 1994—current, John Wiley & Sons; and Kriegler, *Gene Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all. In particular, one can alter the genomic DNA of a wild-type plant by molecular biology techniques that are well-known to one of ordinary skill in the art and generate a recombinant plant. The alteration in the genomic DNA may be a point mutation in a gene which results in an altered the protein sequence, such as pre-mature termination of the protein or the change of one amino acid for another. Alternatively, one can alter the gene such that it fails to undergo transcription into mRNA and/or then translation into a protein.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any changes to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has mutations in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

Once a genetically altered plant has been generated, one can breed it with a wild-type plant and screen for heterozygous F1 generation plants containing the genetic change present in the parent genetically altered plant. Then F2 generation plants can be generated which are homozygous for the mutation. These heterozygous F1 generation plants and homozygous F2 plants, progeny of the original genetically altered plant, are considered genetically altered plants, having the altered genomic material from a parent plant that has been genetically altered.

As discussed briefly above, one can subject a plant's seeds to a mutagen, then grow the seeds, and screen the plants for altered phenotypes. The plants with altered phenotypes will have one or more mutations within the plant's DNA (either within the organelles or nucleus) that cause the altered phenotype. Such genetically altered plants can then be bred as described above to generate homozygous genetically altered plants.

Another way to create mutations in sorghum's Sb06g018040 gene, maize's TS1 gene, and/or Sb06g018040 orthologs from other monocot plants is through genomic editing. Recombinant DNA restriction enzymes can be engineered by fusing a nuclease, for example FokI, with a structure that binds to a site in the MSD2 homologs, as specified by zinc finger, TALEN (transcription activator-like effector nuclease), or by CRISPR (clustered regularly interspaced short palindromic repeat)—Cas9 system, to make a double strand cut within the MSD2 homolog and replace with an engineered nucleic acids identified from the msd2 mutants. FokI is a bacterial type IIS restriction endonuclease consisting of an N-terminal DNA-binding domain, which can be made to bind specific DNA sequences in genome and a non-specific DNA cleavage domain at the C-terminal. See, Belhaj, et al., *Plant Methods* 9(1):39 (2013); Nekrasov, et al., *Nat. Biotechnol.* 31:691-693 (2013); Voytas, D. F., *Annu. Rev. Plant Biol.* 64:327-350 (2013); Shan, et al., *Nat. Biotech.* 31:686-688 (2013); and Li, et al., *Methods* 69(1):9-16 (2014). Genetically altered plants having mutations in Sb06g018040, TS1, and/or orthologs of Sb06g018040 can be selected using marker assisted selection.

Marker-assisted selection is a method of selecting desirable individuals in a breeding scheme based on DNA molecular marker patterns instead of, or in addition to, their phenotypic traits. Marker-assisted selection provides a useful tool that allows for efficient selection of desirable crop traits and is well known in the art (see, e.g., Podlich, et al., *Crop Sci.* 44:1560-1571 (2004), Ribaut and Hoisington, *Trends in Plant Science* 3:236-238 (1998), Knapp, S., *Crop Science* 38:1164-1174 (1998); Hospital, F., *Marker-assisted breeding*, pp 30-59, in *Plant molecular breeding*, H. J. Newbury (ed.), Blackwell Publishing and CRC Press (Oxford and Boca Raton).

As is well known in the art, breeders typically improve crops by crossing plants with desired traits, such as high yield or disease resistance, and selecting the best offspring over multiple generations of testing. Thus, new varieties can easily take eight to ten years to develop. In contrast to conventional selection methods, with marker-assisted selection plants are selected based on molecular marker patterns known to be associated with the traits of interest. Thus, marker-assisted selection involves selecting individuals based on their marker pattern (genotype) rather than their observable traits (phenotype). Thus, molecular marker technology offers the possibility to speed up the selection process and thus offers the potential to develop new cultivars quickly.

Therefore, in an exemplary embodiment, marker assisted selection is used to develop new cereal crops and/or grasses, and, in particular, sorghum cultivars, having the MSD2 phenotype. In this embodiment, the single nucleotide polymorphisms disclosed herein are used as markers to select for the MSD2 phenotype.

In general, the basic procedure for conducting marker assisted selection with DNA markers is as follows: First, extracting DNA from tissue of each individual or family in a population. Second, screening DNA samples via PCR for the molecular marker (SSR, SNP, SCAR, etc.) linked to the trait of interest. Third, separating and scoring PCR products, using an appropriate separation and detection technique. Fourth, identifying individual plants exhibiting or having the desired marker allele. Fifth, combining the marker results with other selection criteria (e.g., phenotypic data or other marker results). Six, selecting the fraction of the population besting meeting the selection criteria, and advancing those selected plant in the breeding program.

The terms "identical" or percent "identity", in the context of two or more nucleic acids or polypeptide sequences, refer to two or more sequences or subsequences that are the same or have a specified percentage of amino acid residues or nucleotides that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or subsequences that have at least about 80%, identity, at least about 81%, 82%, 83%, 84%, 85%/i, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a high percent identity exists over a region of the sequences that is at least about 50 residues in length. In another exemplary embodiment, a high percent identity exists over a region of the sequences that is at least about 100 residues in length. In still another exemplary embodiment, a high percent identity exists over a region of the sequences that is at least about 150 residues or more in length. In one exemplary embodiment, the sequences are high percent identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology,* 1995 supplement).

This invention includes kits that contain at least one pair of polynucleotides which can be used to determine if a plant carries a wild-type or mutated class II 13-lipoxygenase gene where the mutation is a single nucleotide change; optionally a dye for identifying the SNP; optionally a polymerase; and optionally instructions for use of the pair of polynucleotides. One pair of polynucleotides useful for this assay are SEQ ID NO: 13 and SEQ ID NO: 14, where SEQ ID NO: 14 contains the DNA sequence of the wild-typed (non-genetically modified) sequence and SEQ ID NO: 13 contains the single nucleotide mutation (C→T) at nucleotide position 1880 of Sb06g018040 (SEQ ID NO: 1) that results in an mutated class II 13-lipoxygenase that results in reduced amount of 8-cis-jasmonic acid in the genetically altered plant's panicle tissue and thus the AMSD2 phenotype. The second pair of polynucleotides useful for this assay are SEQ ID NO: 15 and SEQ ID NO: 16, where SEQ ID NO: 16 contains the DNA sequence of the wild-typed (non-genetically modified) sequence and SEQ ID NO: 15 contains the single nucleotide mutation (C→T) at nucleotide 2037 of Sb06g018040 (SEQ ID NO: 1) that results in an mutated class II 13-lipoxygenase that results in reduced amount of 8-cis-jasmonic acid in the genetically altered plant's panicle tissue and thus the MSD2 phenotype. During crossing one genetically altered plant expressing the MSD2 phenotype with a non-genetically altered plant into which one wants to breed and express the MSD2 phenotype, one can use the kit to determine which progeny of the cross contains the desired genetic alteration. Thus, methods of using this kit are also included.

In another embodiment of this invention, a kit can contain three polynucleotide primers to distinguish between the SNP containing (genetically altered) plant and the wild-type plant, along with optionally an identifying dye, optionally a polymerase, and optionally instructions. For msd2-1 (p19), one polynucleotide primer has the sequence of SEQ ID NO: 19 which is the wild-type forward primer; one polynucleotide primer has the sequence of SEQ ID NO: 20 which is the SNP forward primer; and one polynucleotide primer has the sequence of SEQ ID NO: 21 which is the reverse primer that is common for both SNP and wild-type sequences. For msd2-2 (p8), one polynucleotide primer has the sequence of SEQ ID NO: 22 which is the wild-type forward primer; one polynucleotide primer has the sequence of SEQ ID NO: 23 (p8) which is the SNP forward primer; and one polynucleotide primer has the sequence of SEQ ID NO: 24 which is the reverse primer that is common for both SNP and wild-type sequences. For msd2-4 (p30), one polynucleotide primer has the sequence of SEQ ID NO: 25 which is the wild-type forward primer; one polynucleotide primer has the sequence of SEQ ID NO: 26 (p30) which is the SNP forward primer; and one polynucleotide primer has the sequence of SEQ ID NO: 27 which is the reverse primer that is common for both SNP and wild-type sequences.

After one obtains a genetically altered plant expressing the MSD2 phenotype, one can efficiently breed the genetically altered plant with other plants containing desired traits. One can use molecular markers (i.e., polynucleotide probes described below) based on the SNP of msd2 gene to determine which offspring of crosses between the genetically altered plant and the other plant have the polynucleotide encoding msd2. This process is known as Marker Assisted Rapid Trait Introgression (MARTI). Briefly, MARTI involves (1) crossing the genetically altered MSD2 plant with a plant line having desired phenotype/genotype ("elite parent") for introgression to obtain F1 offspring. The F1 generation is heterozygous for msd2 gene. (2) Next, an F plant is be backcrossed to the elite parent, producing BC1F1 which genetically produces 50% wild-type and 50% heterozygote msd2 plants. (3) PCR using the polynucleotide probes is performed to select the heterozygote genetically altered plants containing msd2 gene. (4) Selected heterozygotes are then backcrossed to the elite parent to perform further introgression. (5) This process of MARTI is performed for another four cycles. (6) Next, the heterozygote genetically altered plant is self-pollinated by bagging to produce BC6F2 generation. The BC6F2 generation produces a phenotypic segregation ratio of 3 wild-type parent plants to 1 genetically altered MISD2 plant. (7) One selects genetically altered MSD2 plants at the BC6F2 generation at the seedling stage using PCR with the polynucleotide probes and can optionally be combined with phenotypic selection at maturity. These cycles of crossing and selection can be achieved in a span of 2 to 2.5 years (depending on the plant), as compared to many more years for conventional backcrossing introgression method. Thus, the application of MARTI using PCR with polynucleotide probes significantly reduces the time to introgress the AMSD2 genetic alteration into elite lines for producing commercial hybrids. The final product is an inbred plant line almost identical (99%) to the original elite in-bred parent plant that is the homozygous for msd2 gene.

The terms "approximately" and "about" refers to a quantity, level, value or amount that varies by as much as 30/o, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1 Identification of Phenotypic Difference for msd2 Sorghum

From the pedigreed sorghum mutant library created at the Plant Stress and Germplasm Development Research Unit of USDA-ARS at Lubbock, Tex., a series of mutant sorghum plants having coordinated changes of increased number of flower branches, increased size of flower branches, and full fertility of pedicellate spikelets were previously identified. See, Burow et al. (2014); U.S. Patent App. Publication No.: 2014-0068798. The wild-type BTx623, 17 independent msd mutants, including msd2-1 (p19, putative mutant 19), are planted in a field owned by and located at USDA-ARS Agricultural Experiment Station at Lubbock, Tex. (33'39" N, 101'49" W) on May 19, 2012. During late grain filling stage, when the msd phenotype are easily observed, a group of mutated sorghum plants having increased number of flower branches, increases size of flower branches, and full fertility of pedicellate spikelets are identified and isolated. See Burow, et al. (2014) and U.S. Patent App. Publication No.: 2014-0068798. The identified mutated sorghum plants have a potential for three-fold increase in seed number and two-fold increase in seed weight per panicle compared to the wild-type BTx623 sorghum plants. In contrast to the mutated sorghum plant group, for all characterized wild-type sorghum plants, only the sessile spikelets are fertile. It is noteworthy that some phenotypic variations exist between the different MSD mutant sorghum groups. In one group, identified as MSD2, the msd2 sorghum mutants have slightly longer panicle, larger seeds, more open panicles, and greater grain yield than wild-type BTx623 sorghum and msd1 sorghum (msd1 mutant sorghum being described in U.S. Patent Application 62/132,574 filed Mar. 13, 2015). FIG. 1 shows the differences in seed yield phenotype between BTx623, MSD1, and MSD2 sorghum plants. In addition, Table 1 contains more detailed information about the phenotypic differences of MSD2 compared to wild-type BTx623 and MSD1 mutated sorghum. MSD2 has a higher seed yield than BTx623 sorghum and a total seed weight per panicle higher than both BTx623 sorghum and MSD1 sorghum.

TABLE 1

| Traits measured | BTx623 WT | msd1 (p18) | msd2 (p19) |
|---|---|---|---|
| Panicle length (cm) | 25.0 | 32.2 | 37.6 |
| Panicle width (cm) | 8.0 | 9.7 | 13.5 |
| Number of inflorescence nodes | 5.0 | 6.5 | 8.3 |
| Number of primary branches per node | 6.4 | 6.3 | 7.3 |
| Number of seed per primary branch | 65.3 | 148.4 | 130.6 |
| Total number of seed per panicle | 2040 | 5875 | 5869 |
| 100 seed weight (g) | 2.68 | 1.22 | 1.67 |
| Total seed weight per panicle (g) | 54.2 | 67.0 | 93.1 |

Example 2 Identification of Genetic Mutation Producing Observed Phenotype

During late grain filling stage, when the msd phenotype described above is easily observed, leaf samples are collected from each of the confirmed homozygous msd mutants (those plants exhibiting, in the panicles, the multiseed trait described above) to prepare genomic DNA using a method described in Xin and Chen, *Plant Methods* 8:26 (2012). The genomic DNA from BTx623, and seventeen homozygous msd mutants are isolated and sequenced using Illumina HiSeq2000 (San Diego, Calif.) to ~12× coverage of the whole genome by Beijing Genomic Institute, America (Boston, Mass.). Low quality reads, adaptor sequences, and contamination are first excluded from the raw reads. Then the clean reads are aligned to the sorghum reference genome v1.4 with Bowtie2 (Langmead and Salzberg, *Nat. Methods* 9:357-9 (2012)). The SNP calling is performed using Samtools and Bcftools using only the reads with mapping and sequencing quality greater than 20 (Li, et al., *Bioinformatics* 25:2078-9 (2009)). For the parental line BTx623 and individual msd2 mutants, the read depth for true SNPs is set from 3 to 50. Because EMS is known to induce only G/C to A/T transition mutations (Greene, et al., *Genetics* 164:731-40 (2003)), only the homozygous and G/C to A/T SNPs are processed to effect prediction by Ensembl variation predictor (McLaren, et al., *Bioinformatics* 26:2069-70 (2010)). The homology analysis and functional annotation of candidate genes are obtained from Gramene database release 39 (Monaco, et al., *Nucleic Acids Res* 42:D1193-9 (2014)) (gramene.org).

After sequence alignment and SNP calling, the genes that carries nonsynonymous or knockout (non-sense) mutations are annotated and compared among the msd mutants. Seven mutated sorghum plants harbor mutations in the MSD1 gene. Plant #P19 (msd2-1) and other two mutants (msd2-2 (p8) and msd2-3) carry distinct mutations in a gene (Sb06g018040) that has 95% amino acid identity covering 99% of the gene with maize tassel seed 1 (751) (Acosta, et al. (2009)). The genomic sequence of Sb06g018040 is in SEQ ID NO: 1. For msd2-1 (p19), the C→T substitution at position 1880 (based on the genomic sequence) converts the glutamine codon to a stop codon. The genomic sequence of msd2-1 is in SEQ ID NO: 4. For msd2-2 (p8), the C→T substitution at position 2037 (based on the genomic sequence) converts a conserved alanine codon to valine codon. The genomic sequence of msd2-2 is in SEQ ID NO: 7. The msd2-3 allele has the same mutation with msd2-1. The genomic sequence of msd2-3 is in SEQ ID NO: 10. See also FIG. 2 which illustrates the MSD2 gene model and position of the causal SNPs and Table 2.

TABLE 2

| SNP | Mutant | Pos of gene | Variation | Effect | Amino acid change |
|---|---|---|---|---|---|
| 1 | msd2-1 (p19) | 1880 | C/T | stop_gained | Q/* |
| 2 | msd2-2 (p8) | 2037 | C/T | missense_variant | A/V |
| 1 | msd2-3 | 1880 | C/T | stop_gained | Q/* |

The similarity of the mutations in msd2-1 and msd2-3 raises the possibility that these two alleles of msd2 mutants may be siblings. If these two lines are indeed siblings, it is expected that a large portion of the SNPs in the two lines are the same. Based on the information gleaned from the whole genome sequencing data of the two lines, only 4% of the SNPs are identical between the two lines. Thus, the msd2-1 and msd2-3 are not siblings.

To determine if the mutations (SNPs) annotated from the sequencing data are accurate, Kompetitive Allele Specific PCR (KASP) markers (KBioscience/LGC Genomics, Beverly, Mass.) are designed according to the manufacturer's protocols with some modifications and are used to genotype the three mutants to confirm the SNPs. About 200 bp of genomic DNA sequence spanning the causal SNP are submitted to KBioscience/LGC Genomics to design the allele specific primers. The marker amplification and analysis are conducted at the Plant Stress and Germplasm Development Unit at Lubbock, Tex. Briefly, touchdown PCR from 65° C. to 57° C. is used for each pair of primers of the SNPs. After the touchdown step, the PCR amplification continues for 30 cycles using an annealing temperature of 57° C. The resulting PCR products depend on the genotypic state of the sample, whereby WT will only be amplified with a primer with C nucleotide at the ultimate position and thus will incorporate the VIC flourophore, while alternately the mutant genotype will be amplified if the ultimate nucleotide in the primer contains a T, incorporating the FAM fluorophore and providing distinct fluorescent signal for a group of individuals which cluster together at the conclusion of the reaction. All the homozygous msd2-1 mutants have a T at position 1880, while all homozygous msd2-2 mutants have a T at position 2037. These results confirm the annotation from the NGS sequence.

To further confirm the causal SNPs thus identified, co-segregation of the SNPp19 found in msd2-1 with the panicle phenotype are analyzed with 24 individuals F2 plants derived from a cross of BTx623*msd2-1 (p19). The phenotype of the F2 plants is determined with the progeny plants, which provide the ability to distinguish between the homozygous wild-type, heterozygous, and homozygous mutant plants. All expected SNPs are confirmed (see Table 3 below).

TABLE 3

| Mutant ID | SNP1 | SNP2 | SNP3 | SNP4 | SNP5 | SNP-p19 | SNP-p8 |
|---|---|---|---|---|---|---|---|
| msd1-1 | −/− | +/+ | +/+ | +/+ | +/+ | +/+ | +/+ |
| msd1-2 | +/+ | −/− | +/+ | +/+ | +/+ | +/+ | +/+ |
| msd1-3 | +/+ | +/+ | −/− | +/+ | +/+ | +/+ | +/+ |
| msd1-4 | +/+ | +/+ | +/+ | −/− | +/+ | +/+ | +/+ |
| msd1-5 | +/+ | +/+ | +/+ | +/+ | −/− | +/+ | +/+ |
| msd1-6 | −/− | +/+ | +/+ | +/+ | +/+ | +/+ | +/+ |
| msd2-1 (p19) | +/+ | +/+ | +/+ | +/+ | +/+ | −/− | +/+ |
| msd2-2 (p8) | +/+ | +/+ | +/+ | +/+ | +/+ | +/+ | −/− |
| msd2-3 | +/+ | +/+ | +/+ | +/+ | +/+ | −/− | +/+ |
| BTx623 | +/+ | +/+ | +/+ | +/+ | +/+ | +/+ | +/+ |

+/+ indicates homozygous wild-type sequence
−/− indicates homozygous mutant sequence
+/− indicates homozygous heterozygous for the SNP SNP1 to SNP5 correspond to msd1-1 to msd1-5 mutations. The msd1-6 has same SNP as msd1-1. SNPp19 and SNPp8 correspond to msd2-1 and msd2-2 mutations, respectively. The msd2-3 plant has the same SNP mutations as msd2-1 plant. The SNP composition indicates the msd2 alleles contain only the expected mutation in the MSD2 gene. All the SNPs in the MSD1 gene are wild-type sequence in the msd2 mutant alleles. Similarly msd1 mutant alleles contain only mutation in the MSD1 gene and do not contain mutations in the MSD2 gene. The wild-type BTx623 shows wild-type genotype at all SNP sites. This data clearly indicate that AMSD2 and MSD1 are two different genes.

Figure 3:
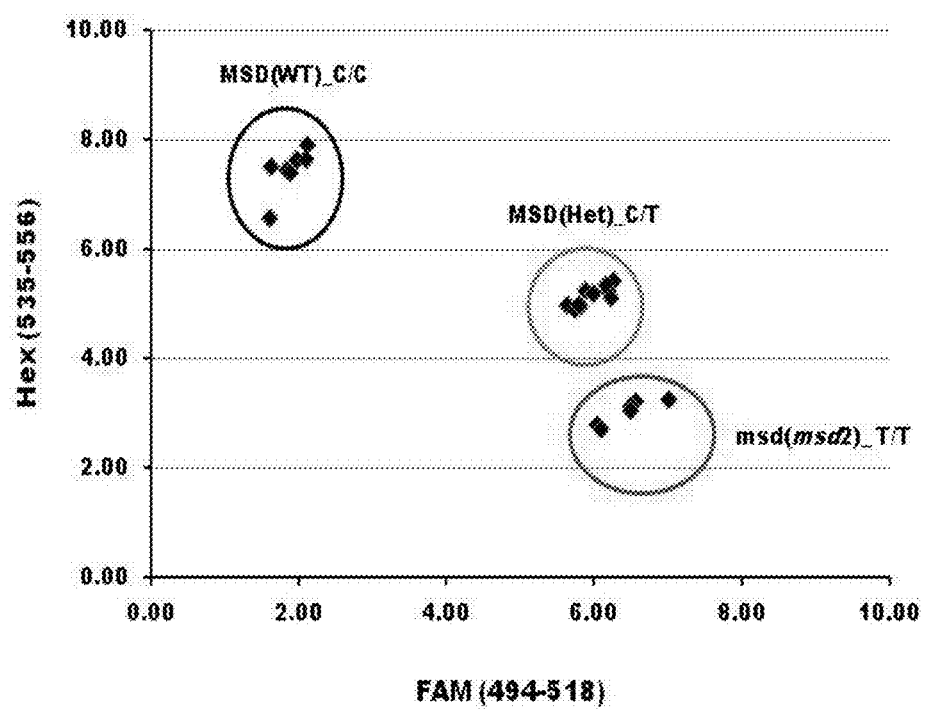
FIG. 3 shows the results of the co-segregation analysis by KASP chemistry of SNP p19 (C→T point mutation) found in Sb06g018040 (msd2 gene) with multiseeded phenotype in a $BC_1F_2$ cross of BTx623_p19 (msd2-1) to BTx623 (WT parent). Genotypic segregation ratio for SNPp19 is 1WT:2Het:1msd2. Each genotype corresponds exactly with the phenotype rating for each member of the population.

Furthermore, the SNPs co-segregated with the SNPs in both backcrossed and outcrossed F2 populations. See FIG. 3 which illustrates the results of a co-segregation analysis of SNPp19 (C→T point mutation) found in Sb06g018040 (msd2 gene) with multiseeded phenotype in a BC$_1$F$_2$cross of BTx623_p19 to BTx623 (WT parent). Genotypic segregation ratio for SNP 7 is 1WT:2Het: 1msd2. Each genotype corresponds exactly with the phenotype rating for each member of the population. KASP chemistry assay is used to obtain this data.

Complementation analysis of msd1 and msd2 mutant alleles is performed. All three msd2 alleles and two msd1 alleles are paired-wise cross-pollinated. Parents used for the crosses are listed at the first row and the first column of Table 4 (below). The phenotype of the F1 plants from the respective crosses is listed in the cell cross-referenced with the parents. When the two parents have mutations in the same gene, the resulting F1 plants are expected to be multiseeded (msd) phenotype, such as the F1 plants from crosses between msd2-1 and msd2-2. When the two parents have mutations in two different genes, the F1 plants are expected to be wild type (WT) because both genes would have a WT copy provided by one of the two parents.

TABLE 4

|  | msd1-1 | msd1-2 | msd2-1 | msd2-2 |
|---|---|---|---|---|
| msd1-1(p12) |  |  |  |  |
| msd1-2 | msd |  |  |  |
| msd2-1(p19) | WT | WT |  |  |
| msd2-2(p8) | WT | WT | msd |  |
| msd2-3 | WT | WT | msd | msd |

WT = wild-type
msd = multiseeded

Three lines of evidence indicate the msd phenotype in msd2 mutants is defined by the mutations in the MSD2 gene and is distinct from that observed in msd1 mutants. Firstly, none of the msd1 SNPs are identified in any of the msd2 mutants, indicating that the MSD1 gene is not mutated in msd2 mutants (see Table 3 supra). Secondly, all F1 plants derived from the crosses among the three msd2 mutants exhibit mutant phenotype, indicating that these three mutants harbor a common mutated gene (see Table 4 supra). Thirdly, the F1 plants from crosses between msd1 and msd2 mutant alleles exhibit the wild type phenotype (See Table 4 supra). Together, these data suggest that the msd1 and the msd2 mutants are caused by mutations on two different genes.

The seeds from homozygous msd2-1 (p19) have been deposited with ATCC under the terms of the Budapest Treaty and accorded Accession Number PTA-121634 (see above).

Example 3 Characterization of the MSD2 Mutation

Based on the sequencing described in Example 2 supra, the amino acid sequence of msd2 (Sb06g018040) parental line BTx623 is in SEQ ID NO: 2, and the coding sequence is in SEQ ID NO: 3. The amino acid sequence of the truncated protein msd2-1 (SNPp19) is in SEQ ID NO: 5, and the coding sequence of msd2-1 (SNPp19) is in SEQ ID NO: 6. The amino acid sequence of the truncated protein msd2-2 (SNPp8) is in SEQ ID NO: 8, and the coding sequence of msd2-2 (SNPp8) is in SEQ ID NO: 9. The amino acid sequence of the truncated protein msd2-3 is in SEQ ID NO: 11, and the coding sequence of msd2-3 is in SEQ ID NO: 12.

Figure 2:
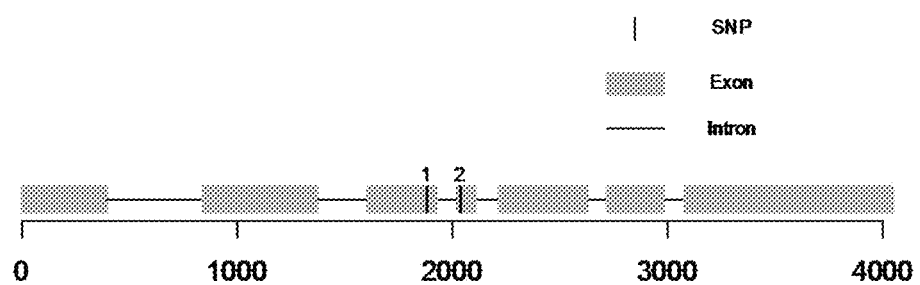
FIG. 2 illustrates the AMSD2 gene model and position of the causal SNPs. The shaded boxes are exons and horizontal lines between the shaded boxes area are intron. The vertical lines and the numbers above the vertical lines are SNPs (mutations) in the msd2 mutant alleles. The SNP labeled "1" is the location of msd2-1 and msd2-3 mutation. The SNP labeled "2" is the location of msd2-2 mutation.
Figure 4:
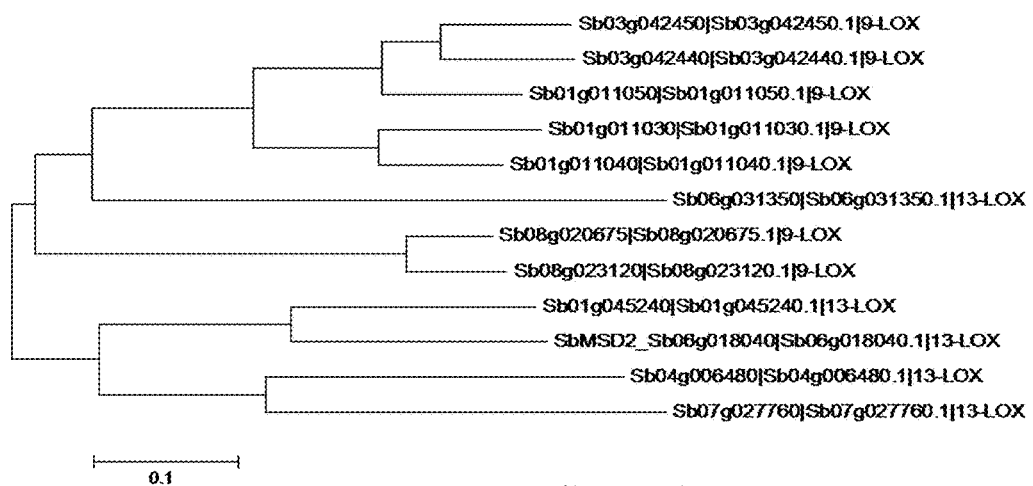
FIG. 4 illustrates the paralogs of lipoxygenases in sorghum genome.

Sequencing analysis indicates that Sb06g018040 encodes class II 13-lipoxygenase (LOX). LOXs are non-heme iron containing fatty acid dioxygenase that catalyze the stereospecific dioxygenation of poly unsaturated fatty acids (Feussner and Wasternack, *Annu. Rev. Plant Biol.* 53:275-297 (2002)). MSD2 belongs to class II 13-LOX that act on the carbon-13 on the fatty acid carbon chain. It is closely related to the maize tassel seed 1 (TS1) (Acosta, et al. (2009)). The two genes have 95% amino acid identity spanning over 99% of the gene. FIG. 2 illustrates the gene structure of Sb06g018040. The gene has 7 exons and 6 introns. The coding sequence (CDS) has 2774 nucleotides (SEQ ID NO: 3) and encodes a protein with 924 amino acids (SEQ ID NO: 2). The maize TS1 gene encodes a type II 13-LOX involved in jasmonic acid biosynthesis and sex determination. Sorghum genome has 12 LOX genes (FIG. 4). The closely related paralog is Sb01g045240. The amino acid identity between these two paralogs is 62% across 97% of the gene, making the MSD2 gene more similar to the TS1 in maize than the paralog in sorghum. Thus, the MSD2 may play a similar role as TS1 in maize to suppress the development of female organs in the pedicellate spikelets.

A metabolite analysis of cis-jasmonic acid in BTx623 sorghum (wild-type) and msd2-1 (SNPp19) and msd2-2 (SNPp8) mutant sorghum is performed. The amount of 8-cis-jasmonic acid in the panicle tissue for msd2-1 is approximately one-third the amount of 8-cis-jasmonic acid in BTx623 sorghum panicle tissue. The amount of 8-cis-jasmonic acid in the panicle tissue for msd2-2 is approximately one-half the amount of 8-cis-jasmonic acid in BTx623 sorghum panicle tissue. However, the amount of 8-cis-jasmonic acid in the leaves of msd2-1 and msd2-2 mutant sorghum are only slightly lower than the amount of 8-cis-jasmonic acid in the leaves of BTx623 sorghum. This analysis helps confirm that Sb06g018040's gene product, class II 13-lipoxygenase, is involved in the biosynthesis of jasmonic acid.

In maize, both tassel and ear are initially bisexual flowers (Chuck, et al., *Nat. Genet.* 39:1517-21 (2007)). Sex determination in maize occurs through abortion of female carpels in the tassel and arrest of male stamens in the ear. Not wishing to be bound to any particular hypothesis, it is possible that the pedicellate spikelets in sorghum also start with both male and female flower organs. At certain stage, the development of the female flower organ is arrested in the pedicellate spikelets. LOXs are known to mediate programmed cell death in both plants and animals (Maccarrone, et al., *Cell Death Differ.* 8:776-784 (2001)). Not wishing to be bound to any particular hypothesis, it is possible that jasmonic acid in the pedicellate spikelets induces programmed cell death leading to the abortion of the pedicellate spikelets. It is unknown at this time why Sb06g018040 does not cause abortion of the sessile spikelets. Again, not wishing to be bound to any particular hypothesis, because both msd1 and msd2 mutants have similar phenotype, they may act in the same pathway that leads to the arrest of the pedicellate spikelets.

Example 4 msd2 Mutation in Other Plants

Figure 5:
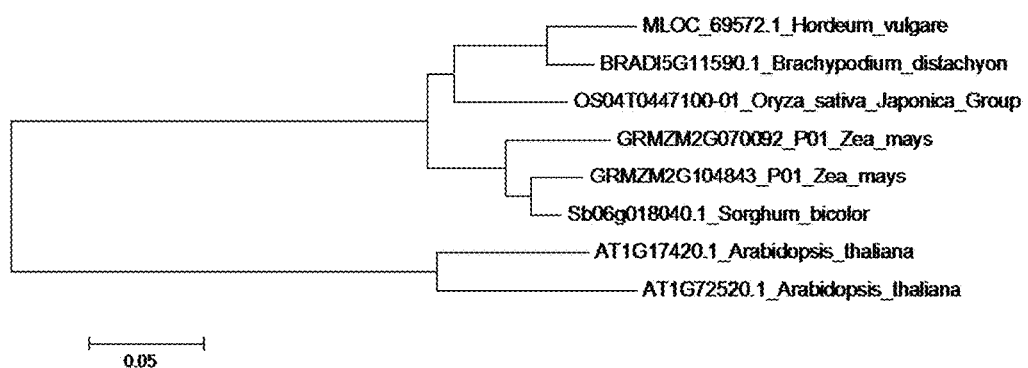
FIG. 5 shows the phylogenetic relationship of MSD2 and its orthologous genes in cereal crops. *Arabidopsis* is included as a reference for dicot plant species.

Using the MSD2 protein sequence, a search of Gramene and NCBI Genbank for orthologous genes in other cereal crops, dicots and fruit/vegetable plants is performed. Two orthologs are identified from maize, one from rice, barley, wheat, pepper, cucumber, tomato, cotton and the Brachypodium genome (FIG. 5). As seen in Table 5 below, the proteins of these genes in cereal crops are at least 84% identical to the amino acid sequence of Sb06g018040 (SEQ ID NO: 2). Ortholog genes in dicot vegetable and fruit plants hold identities lower than 70%. This gene may also affect the flowering in these species (Table 5).

TABLE 5

| Plant | Gene sequences id | % Identity |
|---|---|---|
| Maize (*Zea mays*) | GRMZM2G104843_P01 | 92.19 |
| Maize (*Zea mays*) | GRMZM2G070092_P01 | 87.72 |
| Barley (*Hordeum vulgare*) | MLOC_69572.1 | 84.46 |
| Brachypodium distachyon | BRADI5G11590.1 | 85.19 |
| Rice (*Oryza sativa Japonica*) | OS04T0447100-01 | 90.14 |
| Wheat (*Triticum aestivum*) | Traes_2BL_13328C671.1 | 88.22 |
| Cotton (*Gossypium arboreum*) | gi|728827888 | 64.87 |

TABLE 5-continued

| Plant | Gene sequences id | % Identity |
|---|---|---|
| Pepper (*Capsicum annuum*) | gi|407930085 | 64.43 |
| Cucumber (*Cucumis sativus*) | gi|449447902 | 59.24 |
| Tomato (*Solanum lycopersicum*) | SOLYC03G122340.2 | 63.33 |

When the MSD2 and its orthologous proteins from maize, rice, barley, Brachypodium, and *Arabidopsis* are aligned, both the amino acid glutamine at position 402, which is mutated to a stop codon in msd2-1 and msd2-3, and the alanine at position 423, which is mutated to valine in msd2-2, are conserved in all six genes from the grasses listed in Table 5. Interestingly, all two amino acids mutated in the msd2 alleles are conserved in all the orthologs found in the grass species listed in Table 5. Similar mutations in the orthologous genes from other cereal crops may also lead to increase seed number per plant in the respective crop.

Recombinant plasmids of sgRNA:Cas9 targeting to the rice or wheat MSD2 orthologs are used to bombard rice or wheat callus, respectively using the protocol set forth in Shan, et al. (2013). After binding to the MSD2 ortholog, the Cas9 protein specifically cuts the ortholog's DNA and introduces nucleotide mutations during DNA repair. A few days after the bombardment, mutations in the MSD2 orthologs are screened by PCR. Plant calluses that harbor mutations in the MSD2 ortholog that are expected to have reduced or little activity in the encoded class II 13-LOX protein are induced to regenerate plants for phenotype evaluation. Those genetically altered plants exhibiting msd phenotype of increases flower number and seed numbers are identified.

Example 5 Generation of Sorghum msd2-1 (SNPp19) Breeding Line B.15001msd2-1

The sorghum $F_1$ cross, using the sorghum $F_0$ parent strains indicated in Table 6 below, is made at USDA's research location in Lubbock, Tex., during the summer of 2012. The $F_2$ seeds are obtained during the winter of 2012-13 in a winter nursery in Puerto Vallarta, MX. The $F_2$ population is grown in Lubbock, Tex., during the summer of 2013, and seeds from 40 heads phenotypically classified as MSD2 from the segregation population are bulked together. All plants are self-pollinated. The $F_3$ population containing MSD2 plants is grown in a winter nursery (2013-2014) in Puerto Vallarta, MX. A total of 50 MSD2 plants from the $F_3$ population are selected. All plants were self-pollinated. The $F_4$ families are grown head rows in Lubbock, Tex., in the summer of 2014, and one head is taken from selected rows. The $F_5$ generation are grown and bulked in Guayanilla, PR, in the winter of 2014-2015. The line created is visually confirmed to be true breeding MSD2 in 2015. A summary of the breeding history is in Table 6 below. The criteria for selection at each generation are shown in Table 7 below.

TABLE 6

| Season/Year | Inbreeding | Research Location | Pedigree | Heads Selected |
|---|---|---|---|---|
| S/2012 | $F_0$ | Lubbock, Texas | B.Tx623p19msd/ B.Tx642 | |
| W/2012-13 | $F_1$ | Puerto Vallarta, Mexico | (B.Tx623p19msd/ B.Tx642) | Bulk |
| S/2013 | $F_2$ | Lubbock, Texas | (B.Tx623p19msd/ B.Tx642)-F2 | 40 |

TABLE 6-continued

| Season/Year | Inbreeding | Research Location | Pedigree | Heads Selected |
|---|---|---|---|---|
| W/2013-14 | $F_3$ | Puerto Vallarta, Mexico | (B.Tx623p19msd/ B.Tx642)-F2-F3 | 50 |
| S/2014 | $F_4$ | Lubbock, Texas | (B.Tx623p19msd/ B.Tx642)-F2-F3-1 | 1 |
| W/2014-15 | $F_5$ | Guayanilla, Puerto Rico | (B.Tx623p19msd/ B.Tx642)-F2-F3-1-1 | Bulk |

TABLE 7

| Generation | Traits segregating | Selection Criteria |
|---|---|---|
| $F_1$ | Hybrid or inbred plants | Select $F_1$ hybrids with markers or phenotype |
| $F_2$ | msd, height, maturity | msd marker, moderate height, 50- 70 DAP anthesis |
| $F_3$ | Head type, maturity | semi-open head, early maturity |
| $F_4$ | Head type, uniformity | Representative head |
| $F_5$ | Uniformity, visual confirmation of msd | Bulk random heads | msd2 gene. Two SNP markers for msd2, ARSLBK_SNPp19 and ARSLBK_SNPp8 are listed in Table 8 below. The difference between the SNP mutation sequence and its wild-type sequence are indicated in Table 8 with brackets and in underlined and bolded text. These SNP markers are coupled with endpoint genotyping assay using Kompetitive Allele Specific Primers (KASP) Assay (LGC Genomics, Beverly, Mass.) to rapidly identify and select plants that are heterozygous and homozygous for the msd2 gene among three segregating populations. The SNP genotype markers are efficient in predicting seedlings' phenotype because plant samples are collected very early in plant development, at two to three leaf stage, providing great savings in time, space, effort and cost during actual introgression. These primers provide accuracy towards identification of heterozygous and homozygous msd2 plants. Application of correct gene stacks (for example, when combined with msd1) and rapid msd trait introgression into elite plant lines coupled with KASP SNP marker assay is a valuable application of the discovery of the MSD2 gene and the mutations that give rise to the AMSD2 phenotype. $F_2$ populations of MSD2 (BTx623 trsp19) derived from cross with three different genetic background and segregation ratio for the multi-seeded trait are provided in Table 9.

TABLE 8

| SNP Primer ID | Mutant Target | Sequence (5' to 3') |
|---|---|---|
| ARSLBK_ SNPp19 | msd2-1 | GGCTTCCACGACGTGGACAACCTCTTCAAGGAGGGCCTCCGG CTGAAGCAGGCACTGCAGGACCAGCTGTTCCAGAAGATCCCC TTCGTGCGCAAGATC[T]AGGAGAACAGCGAGGGCCTCCTCCG CTACGACACGCCCGACATCATCAAGAGTAAGCGACCCCCACC CATGATCCATGGA (SEQ ID NO: 13) |
| ARSLBK_ SNPp19 WT | Wild-type | GGCTTCCACCACGTGGACAACCTCTTCAAGGAGGGCCTCCGG CTGAAGCAGGCACTGCAGGACCAGCTGTTCCAGAAGATCCCC TTCGTGCGCAAGATCA[C]AGGAGAACAGCGAGGGCCTCCTCCG CTACGACACGCCCGACATCATCAAGAGTAAGCGACCCCCACC CATGATCCATGGA (SEQ ID NO: 14) |
| ARSLBK_ SNPp8 | msd2-2 | GATTCGATACGATAAGATACGGGGCACGACAATGGTGTGCTC ATGCTGTCATTCTGTGTGGCAGAGGACAAGTTTG[T]GTGGCTG CGCGACGACGAGTTCGCGAGGCAGGCGCTGGCTGGCATCAAC CCCGTCAACATCGAGCGGCTTCAGGTACACATTTCAATCACA AGCCCAACACGC (SEQ ID NO: 15) |
| ARSLBK_ SNPp8 WT | Wild-type | GATTCGATACGATAAGATACGGGGCACGACAATGGTGTGCTC ATGCTGTCATTCTGTGTGGCAGAGGACAAGTTTG[C]GTGGCT GCGCGACGACGAGTTCGCGAGGCAGGCGCTGGCTGGCATCAA CCCCGTCAACATCGAGCGGCTTCAGGTACACATTTCAATCAC AAGCCCAACACGC (SEQ ID NO: 16) |

Example 7. Utilization of MSD2 Single Nucleotide Polymorphism Mutations for Rapid Trait Introgression and Accurate Gene Stacking for Multiseeded Trait Coupled with Marker Assisted Selection Isolation of the multiseeded (msd) mutants and the genes controlling the trait has the potential to increase grain yield in sorghum and other cereal crops. The identification of the nucleotide mutations also led to the development of DNA markers which can be used to screen molecularly altered plants rapidly to improve grain yield. Genetically altered plants can be achieved by rapid introgression of the msd trait and stacking of different alleles of msd2 and various msd genes employing the single nucleotide polymorphism (SNP) primers developed from the nucleotide mutations in the

TABLE 9

| Pedigree | Segregation Ratio (WT:msd) | Genotypic status of trait |
|---|---|---|
| (BTx623p19msd/R.12004)-F2 | 3 WT:1msd | Recessive |
| (BTx623p19msd/R.12030)-F2 | 3 WT:1msd | Recessive |
| (BTx623p19msd/CP_1)-F2 | 3 WT:1msd | Recessive |

Example 8. MSD2 Phenotype Arising from a Non-Functioning Splice Site

Another genetically altered sorghum plant (msd2-4; p30) having the MSD2 phenotype is determined by genomic sequencing to have a G→A mutation at nt 2214 of the gene sequence which destroys the splice site between the third intron and the fourth exon. See SEQ ID NO: 17 for the genomic sequence of this mutation. It is difficult to know the produced protein's sequence with this non-functioning splice site. If a protein is produced, the mutated protein may contain amino acids 1 through 447 from SEQ ID NO: 2 (see also SEQ ID NO: 18 which contains these 447 amino acids) followed by an unknown length of undetermined amino acids. It is also possible that the mRNA will not even be translated. As such, any mutation that results in the loss of the carboxyl 477 amino acids of SEQ ID NO: 2, or more of the carboxyl amino acids, will result in this MSD2 phenotype.

Example 9. SNP Markers and Primers for Identifying MSD2 Mutants

In addition to the primers contained in Table 8 above for distinguishing between the wild-type plants and the genetically altered plants, the primers listed in Table 10, infra, can also be used to distinguish between the wild-type plants and the genetically altered plants. These primers can also be used to identify plants into which the indicated msd2 genetic alteration has been bred. One can use these primers according to the protocols set forth above.

TABLE 10

| GENE ID | Primer ID | Allele_X (5' to 3') (forward primer) | Allele_Y (5' to 3') (forward primer) | Common (5' to 3') (reverse primer) |
|---|---|---|---|---|
| Sb06g018040 | LBK_ARS_Msd2-1 (p19) | GCCCTCGCTGTTCTCCTA (Wild Type) (SEQ ID NO: 19) | GCCCTCGCTGTTCTCCTG (Mutant) (SEQ ID NO: 20) | CCAGCTGTTCCAGAAGATCCGATCC (SEQ ID NO: 21) |
| Sb06g018040 | LBK_ARS_Msd2-2 (p8) | TGGCAGAGGACAAGTTTGC (Wild Type) (SEQ ID NO: 22) | GGCAGAGGACAACTTTGT (Mutant) (SEQ ID NO: 23) | GATGTTGACGGGGTTGATG (SEQ ID NO: 24) |
| Sb06g018040 | LBK_ARS_Msd2-4 (p30) | CCTCGTGTCTCTCTTCCCAG (Wild Type) (SEQ ID NO: 25) | CCTCGTGTCTCTCTTCCCAA (Mutant) (SEQ ID NO: 26) | ATGATGTGCTCCTCCGTGAT (SEQ ID NO: 27) |

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim as follows:

1. A genetically altered sorghum or parts thereof and its progeny having the MSD2 phenotype comprising a genetically altered class II 13-lipoxygenase gene, wherein a wild-type class II 13-lipoxygenase gene comprises SEQ ID NO: 1; wherein said genetically altered class II 13-lipoxygenase gene has a mutation selected from the group consisting of a C→T mutation at nucleotide position 1880 of SEQ ID NO: 1, a C→T mutation at nucleotide position 2037 of SEQ ID NO: 1, a G→A mutation at nucleotide position 2214 of SEQ ID NO: 1, and a null mutation occurring prior to nucleotide position 2214 of SEQ ID NO: 1; wherein said genetically altered class II 13-lipoxygenase has reduced activity or no activity compared to the activity of said wild-type class II 13-lipoxygenase; and wherein said reduced activity or said no activity of said genetically altered class II 13-lipoxygenase causes said MSD2 phenotype.

2. The genetically altered sorghum or parts thereof and its progeny of claim 1, wherein said genetically altered class II 13-lipoxygenase comprises the amino acid sequence selected from the group consisting of SEQ ID NO: 5, SEQ ID NO: 8, and SEQ ID NO: 18.

3. The genetically altered sorghum of claim 1 wherein said sorghum plant has ATCC Accession Number PTA-121634.

4. A genetically altered cell from the genetically altered sorghum of claim 1 comprising said genetically altered class II 13-lipoxygenase gene.

5. A tissue culture comprising a plurality of said genetically altered cells of claim 4.

6. A genetically altered seed from the genetically altered sorghum of claim 1 comprising said genetically altered class II 13-lipoxygenase gene.

7. A genetically altered pollen from the genetically altered sorghum of claim 1 comprising said genetically altered class II 13-lipoxygenase gene.

8. A genetically altered sorghum comprising an altered class II 13-lipoxygenase protein with reduced activity compared to the activity of a wild-type class II 13-lipoxygenase protein, wherein said wild-type class II 13-lipoxygenase protein is encoded by SEQ ID NO: 3; wherein said altered class II 13-lipoxygenase protein has a sequence consisting of SEQ ID NO: 6, SEQ ID NO: 9, or amino acids 1 through 447 of SEQ ID NO: 2; and wherein said genetically altered sorghum expresses MSD2 phenotype.

9. A genetically altered cell from the genetically altered sorghum of claim 8 comprising said altered class II 13-lipoxygenase protein.

10. A genetically altered tissue culture comprising a plurality of said genetically altered cells of claim 9.

11. A genetically altered seed from the genetically altered sorghum of claim 8 comprising said altered class II 13-lipoxygenase protein.

12. A genetically altered pollen from the genetically altered sorghum of claim 8 comprising said altered class II 13-lipoxygenase protein.

13. A method for constructing the genetically altered sorghum plant of claim 8, the method comprising:
  (i) introducing an altered nucleic acid into a wild-type sorghum cell to provide a genetically altered sorghum cell, wherein said altered nucleic acid encodes an altered class II 13-lipoxygenase protein having a sequence consisting of SEQ ID NO: 6, SEQ ID NO: 9, or amino acids 1 through 447 of SEQ ID NO: 2;
  (ii) selecting the genetically altered sorghum cell that produces said altered class II 13-lipoxygenase protein;
  (iii) allowed said selected genetically altered sorghum cell to grow into a genetically altered sorghum that produces said altered class II 13-lipoxygenase.

14. The method of claim 13, wherein said introducing said altered nucleic acid occurs via introgression, genomic editing, or exposing said sorghum to a mutagen, and said selecting said genetically altered sorghum occurs via marker assisted selection.

15. The method of claim 13, wherein said altered class II 13-lipoxygenase produces reduced amount of 8-cis-jasmonic acid in said genetically altered sorghum's panicle tissue compared to the amount of 8-cis-jasmonic acid in a sorghum's panicle tissue.

* * * * *

SEQUENCE LISTING

<160> NUMBER OF SEQ ID NOS: 27

<210> SEQ ID NO 1
<211> LENGTH: 4048
<212> TYPE: DNA
<213> ORGANISM: Sorghum bicolor

<400> SEQUENCE: 1

```
atggcgtcgg cgatggagct ggttgggaga tctttcttgc cgggctctgc cgccgcggcg      60
tcgccggcgg gccgggagcg gcggcgaggc gggccctgct tcgccgcggt cggaagggag     120
gggagtgcgc acaagcggcg gccgtcgctg aggtcgaccg cgccggtggg cgcgctggcc     180
gagcgcgtcg tggtgacccc ggcgccgccg gaggagaggg ccgggacggc cccgccggag     240
ccgcacccgc agagcgtggc cgcgcgcgcc gtggtcaccg tgcggcggag gcgcaaggag     300
gacgccaagc gccgcgtcgc cgagcagctg gacgcctacg ccgacagggt cggccgcagc     360
gtcctcctcg agctcatcag cacggagacc gacccaagta agaaacattt cttccgtgat     420
cccacctcca ccaccccac cgccgccgcc gccgccgcgc gacggcatgg aattccatgg     480
```

-continued

```
cgcatccggc gggcggttgc gttgcatctt tgaattgtat gctactagca gtagcacaat    540
ttggttccat tttcttctct cctcctcgcc cttttttcca ttccactcgc cgctccttca    600
ccttcatgga aacccgcgcg cggcgagaat attccagctg gtgcgccttg acgtctgggg    660
cctctgtctc cgagtcatca tctccaaatg gaccatcacg tggagctgtc tctcttgatt    720
tgatttctgc caaaagccgc cgtctttacc gtctcctcgg cgtcgaaacg gaaatggaac    780
gaattttact tacgcctggc ggcgagcatt cacctgacga tcgaaatgaa ttggtggcag    840 gaaaagggg ccccaagaag agccggcggt cggcgctggt ggggtggttc gagaagaagg    900
acgtcaaggc ggagcgggtg gtgtacacgg cggacttcac cgtcgacggg tgcttcggcg    960
agcctggcgc cgtcaccgtg ctcaaccggc accagcgcga gttcttcatc gagagcatcg   1020
tggtggaggg cttccctcg ggccccgcgc acttcacctg caactcgtgg gtgcagccca    1080
cccgcgtgga ccgcaacccg cgcgtgttct tcaccaacaa gccctacctg ccggccgaga   1140
cgccgccggg gctgcaggag ctccgccgcc aggagctcag cgacctgagg ggcgagggcg   1200
gcgccgacac caccggcgag cgcaggatca ccgaccgggt gtgggagtac gacgtgtaca   1260
acgacctcgg caacccggac aagggcgccg agttcgcgcg cccgatcctc ggcggcgagc   1320
agcagctgcc gtacccgcgc cggatgcgaa cgggccggcc caagaccttc acaggtgcag   1380
cctccctctc cgcttttcaat tcccctctca ctcttcactt cttgtcacca ccgccgtccg   1440
ccccataaat cccgcgacag taactgtggc cgaccggaca cggcggaggt cgccgtcgcg   1500
cgtagctttc gtatcgaaac cacccgatcg cgggcgacgt tgaccgaccg acgctaacat   1560
ttcgtcacgc acgcacggtg cttgctgctt tgcttgctcg ctcgcagacg atcgcgcgga   1620
gagcagggtg gagtacccgg agcccatcta cgtgtcccgg gacgaggagt tcgaggaggg   1680
caagaacgag atgctgtcgg agggcgcgct caaggcgctg ctccacaact tcatgccgct   1740
gctggtgagc tccgtgtcgc cggacatccg cgacttcgcc ggcttccacg acgtggacaa   1800
cctcttcaag gagggcctcc ggctgaagca ggcactgcag gaccagctgt tccagaagat   1860
ccccttcgtg cgcaagatcc aggagaacag cgagggcctc ctccgctacg acacgcccga   1920
catcatcaag agtaagcgac ccccacccat gatccatgga gattcgatac gataagatac   1980
ggggcacgac aatggtgtgc tcatgctgtc attctgtgtg gcagaggaca agtttgcgtg   2040
gctgcgcgac gacgagttcg cgaggcaggc gctggctggc atcaacccc gtcaacatcga   2100 gcggcttcag gtacacattt caatcacaag cccaacacgc cgcggacatt gagactacac   2160
gtccactgct cgctcatctc actgccgttc gtttcctcgt gtctctcttc ccaggcgttc   2220
ccgccgatga gcaagctgga cccggccgtg tacggcccgc cggagtcggc catcacggag   2280
gagcacatca tcgggcagct ggacggcatg tcggtgcggc aggcgctgca ggacaaccgg   2340
ctgtacatgc tggactacca cgacatcttc ctgccgttcc tggaccggat caacgcgcag   2400
gacgggcgga aggcctacgg cacgcgcacg ctcttcttcc tgacggcggc gggcacgctc   2460
aagcccatcg ccatcgagct gtgcctgccg cccatgaccg acgggtgcgc gcgcgccaag   2520
cgggtgttca cgccgcccgc cgacgccacc agcaactggc tgtggcagct cgccaaggcg   2580
cacgtctgct ccaacgacgc cggcgtccac cagctcatca accactggta cgacacgaca   2640
ctgtctgtgt cagtcttgca ggaggaggca atctcaaagt caaaagtgtt ggattccact   2700
gatcatgagt tgtgccaggc tgaggacgca cgcgtgcatg gagccgttca tcatctcggc   2760
gcaccggcag ctgagcgcga tgcacccat cttcaagctg ctcaagccgc acatgcgcta   2820
cacgctcaag atcaacgcgc tggcgcggca gatcctcatc aacggcgacg gcgtcatcga   2880
```

-continued

```
gtccggcttc accccggcc gctactgcat ggagatgagc tcgttcgcgt accaggagct    2940
ctggcggctc gaccaggagg gcctccctgc cgatctcatc agaaggtaca cagatcaatc    3000
aatcacatga agttgtgat gcttcgtgcg atgcaatggt gcttgctgac atgggtgttt    3060
tctttgtcac aacacagagg aatggccgtg gaggacccga cgcagccgca cggtctccgg    3120
ctgctgatcg aggactaccc gtacgccacc gacgggctgc tcctctggga cgccatcacg    3180
cggtggtgcg acgcgtacgt ggccatgtac tacccgtccg accaagccgt gcagggcgac    3240
acggagctgc agtcgtggta cagggaggcg gtgcagacgg ggcacgcgga caagcgcggc    3300
gcgccgtggt ggccgcgcct gtcgacgccg ggcgacctgg cgtcgctgct caccacgctg    3360
ctgtggctca cctcggcgca gcacgcggcg ctcaacttcg ggcagtaccc gctgggcggc    3420
tacatcccga accgaccgcc gctcatgcgg cggctggtgc cgccgacgg cgacccggag    3480 tacgcgcacc tggtggccga cccgcaccgc ttcttcctgt cggcgctgcc cagcctgacg    3540
cagacgacca ccttcatgac cgtcatcgac acgctgtcca cgcactccgc cgacgagcag    3600
tacctcgggg agcggcccga cgaggcgtgg acggccgacc cggcggcgct ggcggcggcg    3660
cgcgagttcg cggacgaggt gcgccgcgcc gaggaggaga tcgaccggcg caacgcggac    3720
acgggacgcc gcaaccggtg cggcgccggc gtgctgccgt acgagctcat ggcgcccacg    3780
tccgggccgg gcatcacctg ccgcggcatc cccaacagcg tcaccattta gtctctcgcg    3840
gtaccgatag ccatgggaga aatctaagca gaagcaaaat gatttttttt ttgctttact    3900
tctcccccat tgccaaattg ccattgattt ggaggtctga acaggtggag tttgattttt    3960
gactagggga gagacactga ggaactgaat gggtgtaaat aatttgttat tatagaaaaa    4020
aaatcaatga aatataatca ttagagtt                                      4048
```

<210> SEQ ID NO 2
<211> LENGTH: 924
<212> TYPE: PRT
<213> ORGANISM: Sorghum bicolor

<400> SEQUENCE: 2

```
Met Ala Ser Ala Met Glu Leu Val Gly Arg Ser Phe Leu Pro Gly Ser
1               5                   10                  15

Ala Ala Ala Ala Ser Pro Ala Gly Arg Glu Arg Arg Gly Gly Pro
            20                  25                  30

Cys Phe Ala Ala Val Gly Arg Glu Gly Ser Ala His Lys Arg Arg Pro
        35                  40                  45

Ser Leu Arg Ser Thr Ala Pro Val Gly Ala Leu Ala Glu Arg Val Val
    50                  55                  60

Val Thr Pro Ala Pro Glu Glu Arg Ala Gly Thr Ala Pro Pro Glu
65                  70                  75                  80

Pro His Pro Gln Ser Val Ala Ala Arg Ala Val Thr Val Arg Arg
                85                  90                  95

Arg Arg Lys Glu Asp Ala Lys Arg Arg Val Ala Glu Gln Leu Asp Ala
            100                 105                 110

Tyr Ala Asp Arg Val Gly Arg Ser Val Leu Leu Glu Leu Ile Ser Thr
        115                 120                 125

Glu Thr Asp Pro Arg Lys Gly Gly Pro Lys Lys Ser Arg Arg Ser Ala
    130                 135                 140

Leu Val Gly Trp Phe Glu Lys Lys Asp Val Lys Ala Glu Arg Val Val
145                 150                 155                 160
```

```
Tyr Thr Ala Asp Phe Thr Val Asp Gly Cys Phe Gly Glu Pro Gly Ala
                165                 170                 175

Val Thr Val Leu Asn Arg His Gln Arg Glu Phe Phe Ile Glu Ser Ile
            180                 185                 190

Val Val Glu Gly Phe Pro Ser Gly Pro Ala His Phe Thr Cys Asn Ser
        195                 200                 205

Trp Val Gln Pro Thr Arg Val Asp Arg Asn Pro Arg Val Phe Phe Thr
    210                 215                 220

Asn Lys Pro Tyr Leu Pro Ala Glu Thr Pro Pro Gly Leu Gln Glu Leu
225                 230                 235                 240

Arg Arg Gln Glu Leu Ser Asp Leu Arg Gly Glu Gly Ala Asp Thr
                245                 250                 255

Thr Gly Glu Arg Arg Ile Thr Asp Arg Val Trp Glu Tyr Asp Val Tyr
            260                 265                 270

Asn Asp Leu Gly Asn Pro Asp Lys Gly Ala Glu Phe Ala Arg Pro Ile
        275                 280                 285

Leu Gly Gly Glu Gln Gln Leu Pro Tyr Pro Arg Arg Met Arg Thr Gly
    290                 295                 300

Arg Pro Lys Thr Phe Thr Asp Arg Ala Glu Ser Arg Val Glu Tyr
305                 310                 315                 320

Pro Glu Pro Ile Tyr Val Ser Arg Asp Glu Glu Phe Glu Glu Gly Lys
                325                 330                 335

Asn Glu Met Leu Ser Glu Gly Ala Leu Lys Ala Leu Leu His Asn Phe
            340                 345                 350

Met Pro Leu Leu Val Ser Ser Val Ser Pro Asp Ile Arg Asp Phe Ala
        355                 360                 365

Gly Phe His Asp Val Asp Asn Leu Phe Lys Glu Gly Leu Arg Leu Lys
    370                 375                 380

Gln Ala Leu Gln Asp Gln Leu Phe Gln Lys Ile Pro Phe Val Arg Lys
385                 390                 395                 400

Ile Gln Glu Asn Ser Glu Gly Leu Leu Arg Tyr Asp Thr Pro Asp Ile
                405                 410                 415

Ile Lys Lys Asp Lys Phe Ala Trp Leu Arg Asp Asp Glu Phe Ala Arg
            420                 425                 430

Gln Ala Leu Ala Gly Ile Asn Pro Val Asn Ile Glu Arg Leu Gln Ala
        435                 440                 445

Phe Pro Pro Met Ser Lys Leu Asp Pro Ala Val Tyr Gly Pro Pro Glu
    450                 455                 460

Ser Ala Ile Thr Glu Glu His Ile Ile Gly Gln Leu Asp Gly Met Ser
465                 470                 475                 480

Val Arg Gln Ala Leu Gln Asp Asn Arg Leu Tyr Met Leu Asp Tyr His
                485                 490                 495

Asp Ile Phe Leu Pro Phe Leu Asp Arg Ile Asn Ala Gln Asp Gly Arg
            500                 505                 510

Lys Ala Tyr Gly Thr Arg Thr Leu Phe Phe Leu Thr Ala Ala Gly Thr
        515                 520                 525

Leu Lys Pro Ile Ala Ile Glu Leu Cys Leu Pro Pro Met Thr Asp Gly
    530                 535                 540

Cys Ala Arg Ala Lys Arg Val Phe Thr Pro Ala Asp Ala Thr Ser
545                 550                 555                 560

Asn Trp Leu Trp Gln Leu Ala Lys Ala His Val Cys Ser Asn Asp Ala
                565                 570                 575

Gly Val His Gln Leu Ile Asn His Trp Leu Arg Thr His Ala Cys Met
```

580                 585                 590
Glu Pro Phe Ile Ile Ser Ala His Arg Gln Leu Ser Ala Met His Pro
                595                 600                 605

Ile Phe Lys Leu Leu Lys Pro His Met Arg Tyr Thr Leu Lys Ile Asn
            610                 615                 620

Ala Leu Ala Arg Gln Ile Leu Ile Asn Gly Asp Gly Val Ile Glu Ser
625                 630                 635                 640

Gly Phe Thr Pro Gly Arg Tyr Cys Met Glu Met Ser Ser Phe Ala Tyr
                645                 650                 655

Gln Glu Leu Trp Arg Leu Asp Gln Glu Gly Leu Pro Ala Asp Leu Ile
            660                 665                 670

Arg Arg Gly Met Ala Val Glu Asp Pro Thr Gln Pro His Gly Leu Arg
                675                 680                 685

Leu Leu Ile Glu Asp Tyr Pro Tyr Ala Thr Asp Gly Leu Leu Leu Trp
            690                 695                 700

Asp Ala Ile Thr Arg Trp Cys Asp Ala Tyr Val Ala Met Tyr Tyr Pro
705                 710                 715                 720

Ser Asp Gln Ala Val Gln Gly Asp Thr Glu Leu Gln Ser Trp Tyr Arg
                725                 730                 735

Glu Ala Val Gln Thr Gly His Ala Asp Lys Arg Gly Ala Pro Trp Trp
            740                 745                 750

Pro Arg Leu Ser Thr Pro Gly Asp Leu Ala Ser Leu Leu Thr Thr Leu
                755                 760                 765

Leu Trp Leu Thr Ser Ala Gln His Ala Ala Leu Asn Phe Gly Gln Tyr
            770                 775                 780

Pro Leu Gly Gly Tyr Ile Pro Asn Arg Pro Pro Leu Met Arg Arg Leu
785                 790                 795                 800

Val Pro Ala Asp Gly Asp Pro Glu Tyr Ala His Leu Val Ala Asp Pro
                805                 810                 815

His Arg Phe Phe Leu Ser Ala Leu Pro Ser Leu Thr Gln Thr Thr Thr
            820                 825                 830

Phe Met Thr Val Ile Asp Thr Leu Ser Thr His Ser Ala Asp Glu Gln
            835                 840                 845

Tyr Leu Gly Glu Arg Pro Asp Glu Ala Trp Thr Ala Asp Pro Ala Ala
        850                 855                 860

Leu Ala Ala Ala Arg Glu Phe Ala Asp Glu Val Arg Arg Ala Glu Glu
865                 870                 875                 880

Glu Ile Asp Arg Arg Asn Ala Asp Thr Gly Arg Arg Asn Arg Cys Gly
                885                 890                 895

Ala Gly Val Leu Pro Tyr Glu Leu Met Ala Pro Thr Ser Gly Pro Gly
            900                 905                 910

Ile Thr Cys Arg Gly Ile Pro Asn Ser Val Thr Ile
        915                 920

<210> SEQ ID NO 3
<211> LENGTH: 2774
<212> TYPE: DNA
<213> ORGANISM: Sorghum bicolor

<400> SEQUENCE: 3
atggcgtcgg cgatggagct ggttgggaga tctttcttgc cgggctctgc cgccgcggcg     60
tcgccggcgg gccgggagcg gcggcgaggc gggccctgct cgccgcggt cggaagggag    120 gggagtgcgc acaagcggcg gccgtcgctg aggtcgaccg cgccggtggg cgcgctggcc    180

```
gagcgcgtcg tggtgacccc ggcgccgccg gaggagaggg ccgggacggc cccgccggag    240
ccgcacccgc agagcgtggc cgcgcgcgcc gtggtcaccg tgcggcggag cgcaaggag    300 gacgccaagc gccgcgtcgc cgagcagctg gacgcctacg ccgacagggt cggccgcagc    360
gtcctcctcg agctcatcag cacggagacc gacccaagaa aaggggggccc caagaagagc    420 cggcggtcgg cgctggtggg gtggttcgag aagaaggacg tcaaggcgga gcggtggtg     480 tacacggcgg acttcaccgt cgacgggtgc ttcggcgagc ctggcgccgt caccgtgctc    540
aaccggcacc agcgcgagtt cttcatcgag agcatcgtgg tggagggctt ccctcgggc    600 cccgcgcact tcacctgcaa ctcgtgggtg cagcccaccc gcgtggaccg caacccgcgc    660
gtgttcttca ccaacaagcc ctacctgccg gccgagacgc cgccggggct gcaggagctc    720
cgccgccagg agctcagcga cctgaggggc gagggcggcg ccgacaccac cggcgagcgc    780
aggatcaccg accgggtgtg ggagtacgac gtgtacaacg acctcggcaa cccggacaag    840
ggcgccgagt tcgcgcgccc gatcctcggc ggcgagcagc agctgccgta cccgcgccgg    900
atgcgaacgg gccggcccaa gaccttcaca gacgatcgcg cggagagcag ggtggagtac    960
ccggagccca tctacgtgtc ccgggacgag gagttcgagg agggcaagaa cgagatgctg   1020
tcggagggcg cgctcaaggc gctgctccac aacttcatgc cgctgctggt gagctccgtg   1080
tcgccggaca tccgcgactt cgccggcttc cacgacgtgg acaacctctt caaggagggc   1140
ctccggctga agcaggcact gcaggaccag ctgttccaga agatcccctt cgtgcgcaag   1200
atccaggaga acagcgaggg cctcctccgc tacgacacgc ccgacatcat caagaaggac   1260
aagtttgcgt ggctgcgcga cgacgagttc gcgaggcagg cgctggctgg catcaacccc   1320
gtcaacatcg agcggcttca ggcgttcccg ccgatgagca agctggaccc ggccgtgtac   1380
ggcccgccgg agtcggccat cacggaggag cacatcatcg ggcagctgga cggcatgtcg   1440
gtgcggcagg cgctgcagga caaccggctg tacatgctgg actaccacga catcttcctg   1500
ccgttcctgg accggatcaa cgcgcaggac gggcggaagg cctacggcac gcgcacgctc   1560
ttcttcctga cggcggcggg cacgctcaag cccatcgcca tcgagctgtg cctgccgccc   1620
atgaccgacg ggtgcgcgcg cgccaagcgg gtgttcacgc cgcccgccga cgccaccagc   1680
aactggctgt ggcagctcgc caaggcgcac gtctgctcca cgacgccgg cgtccaccag    1740 ctcatcaacc actggctgag gacgcacgcg tgcatggagc cgttcatcat ctcggcgcac   1800
cggcagctga gcgcgatgca ccccatcttc aagctgctca gccgcacat gcgctacacg    1860 ctcaagatca cgcgctggc gcggcagatc ctcatcaacg cgacggcgt catcgagtcc    1920 ggcttcaccc ccggccgcta ctgcatggag atgagctcgt tcgcgtacca ggagctctgg   1980
cggctcgacc aggagggcct ccctgccgat ctcatcagaa aggaatggc cgtggaggac   2040 ccgacgcagc cgcacggtct ccggctgctg atcgaggact acccgtacgc cacccgacggg   2100 ctgctcctct gggacgccat cacgcggtgg tgcgacgcgt acgtggccat gtactacccg   2160
tccgaccaag ccgtgcaggg cgacacggag ctgcagtcgt ggtacaggga ggcggtgcag   2220
acggggcacg cggacaagcg cggcgcgccg tggtggccgc gcctgtcgac gccgggcgac   2280
ctggcgtcgc tgctcaccac gctgctgtgg ctcacctcgg cgcagcacgc ggcgctcaac   2340
ttcgggcagt acccgctggg cggctacatc ccgaaccgac cgccgctcat gcggcggctg   2400
gtgcccgccg acggcgaccc ggagtacgcg cacctggtgg ccgacccgca ccgcttcttc   2460
ctgtcggcgc tgcccagcct gacgcagacg accaccttca tgaccgtcat cgacacgctg   2520
tccacgcact ccgccgacga gcagtacctc ggggagcggc ccgacgaggc gtggacggcc   2580
```

```
gacccggcgg cgctggcggc ggcgcgcgag ttcgcggacg aggtgcgccg cgccgaggag    2640
gagatcgacc ggcgcaacgc ggacacggga cgccgcaacc ggtgcggcgc cggcgtgctg    2700
ccgtacgagc tcatggcgcc cacgtccggg ccgggcatca cctgccgcgg catccccaac    2760
agcgtcacca ttta                                                      2774

<210> SEQ ID NO 4
<211> LENGTH: 4048
<212> TYPE: DNA
<213> ORGANISM: Sorghum bicolor

<400> SEQUENCE: 4
atggcgtcgg cgatggagct ggttgggaga tctttcttgc cgggctctgc cgccgcggcg     60
tcgccggcgg gccgggagcg gcggcgaggc gggccctgct cgccgcggt cggaagggag    120 gggagtgcgc acaagcggcg gccgtcgctg aggtcgaccg cgccggtggg cgcgctggcc    180
gagcgcgtcg tggtgacccc ggcgccgccg aggagaggg ccgggacggc cccgccggag    240
ccgcacccgc agagcgtggc cgcgcgcgcc gtggtcaccg tgcggcggag gcgcaaggag    300
gacgccaagc gccgcgtcgc cgagcagctg acgcctacg ccgacagggt cggccgcagc    360
gtcctcctcg agctcatcag cacggagacc gacccaagta agaaacattt cttccgtgat    420
cccacctcca ccaccccac cgccgccgcc gccgccgcgc gacggcatgg aattccatgg    480
cgcatccggc gggcggttgc gttgcatctt tgaattgtat gctactagca gtagcacaat    540
ttggttccat tttcttctct cctcctcgcc ctttttcca ttccactcgc cgctccttca    600
ccttcatgga aaccgcgcg cggcgagaat attccagctg gtgcgccttg acgtctgggg    660
cctctgtctc cgagtcatca ctccaaatg gaccatcacg tggagctgtc tctcttgatt    720
tgatttctgc caaaagccgc cgtctttacc gtctcctcgg cgtcgaaacg gaaatggaac    780
gaattttact tacgcctggc ggcgagcatt cacctgacga tcgaaatgaa ttggtggcag    840 gaaaagggggg ccccaagaag agccggcggt cggcgctggt ggggtggttc gagaagaagg    900
acgtcaaggc ggagcgggtg gtgtacacgc cggacttcac cgtcgacggg tgcttcggcg    960
agcctggcgc cgtcaccgtg ctcaaccggc accagcgcga gttcttcatc gagagcatcg   1020
tggtggaggg cttttccctcg ggccccgcgc acttcacctg caactcgtgg gtgcagccca   1080
cccgcgtgga ccgcaacccg cgcgtgttct tcaccaacaa gccctacctg ccggccgaga   1140
cgccgccggg gctgcaggag ctccgccgcc aggagctcag cgacctgagg ggcgagggcg   1200
gcgccgacac caccggcgag cgcaggatca ccgaccgggt gtgggagtac gacgtgtaca   1260
acgacctcgg caacccggac aagggcgccg agttcgcgcg cccgatcctc ggcggcgagc   1320
agcagctgcc gtaccgcgc cggatgcgaa cgggccggcc caagaccttc acaggtgcag   1380
cctccctctc cgcttttcaat tccctctca ctcttcactt cttgtcacca ccgccgtccg   1440
ccccataaat cccgcgacag taactgtggc cgaccggaca cggcggaggt cgccgtcgcg   1500
cgtagctttc gtatcgaaac cacccgatcg cgggcgacgt tgaccgaccg acgctaacat   1560
ttcgtcacgc acgcacggtg cttgctgctt tgcttgctcg ctcgcagacg atcgcgcgga   1620
gagcagggtg gagtacccgg agcccatcta cgtgtcccgg gacgaggagt cgaggaggg   1680 caagaacgag atgctgtcgg agggcgcgct caaggcgctg ctccacaact tcatgccgct   1740
gctggtgagc tccgtgtcgc cggacatccg cgacttcgcc ggcttccacg acgtggacaa   1800
cctcttcaag gagggcctcc ggctgaagca ggcactgcag gaccagctgt tccagaagat   1860
```

```
cccccttcgtg cgcaagatct aggagaacag cgagggcctc ctccgctacg acacgcccga   1920
catcatcaag agtaagcgac ccccacccat gatccatgga gattcgatac gataagatac   1980
ggggcacgac aatggtgtgc tcatgctgtc attctgtgtg gcagaggaca agtttgcgtg   2040
gctgcgcgac gacgagttcg cgaggcaggc gctggctggc atcaaccccg tcaacatcga   2100
gcggcttcag gtacacattt caatcacaag cccaacacgc cgcggacatt gagactacac   2160
gtccactgct cgctcatctc actgccgttc gtttcctcgt gtctctcttc ccaggcgttc   2220
ccgccgatga gcaagctgga cccggccgtg tacgcccgc cggagtcggc catcacggag    2280
gagcacatca tcgggcagct ggacggcatg tcggtgcggc aggcgctgca ggacaaccgg   2340
ctgtacatgc tggactacca cgacatcttc ctgccgttcc tggaccggat caacgcgcag   2400
gacgggcgga aggcctacgg cacgcgcacg ctcttcttcc tgacggcggc gggcacgctc   2460
aagcccatcg ccatcgagct gtgcctgccg cccatgaccg acgggtgcgc gcgcgccaag   2520
cgggtgttca cgccgcccgc cgacgccacc agcaactggc tgtggcagct cgccaaggcg   2580
cacgtctgct ccaacgacgc cggcgtccac cagctcatca accactggta cgacacgaca   2640
ctgtctgtgt cagtcttgca ggaggaggca atctcaaagt caaaagtgtt ggattccact   2700
gatcatgagt tgtgccaggc tgaggacgca cgcgtgcatg gagccgttca tcatctcggc   2760
gcaccggcag ctgagcgcga tgcaccccat cttcaagctg ctcaagccgc acatgcgcta   2820
cacgctcaag atcaacgcgc tggcgcggca gatcctcatc aacggcgacg cgtcatcga   2880 gtccggcttc accccggcc gctactgcat ggagatgagc tcgttcgcgt accaggagct   2940
ctggcggctc gaccaggagg gcctcccctgc cgatctcatc agaaggtaca cagatcaatc   3000
aatcacatga agttgtgat gcttcgtgcg atgcaatggt gcttgctgac atgggtgttt   3060
tctttgtcac aacacagagg aatggccgtg gaggacccga cgcagccgca cggtctccgg   3120
ctgctgatcg aggactaccc gtacgccacc gacgggctgc tcctctggga cgccatcacg   3180
cggtggtgcg acgcgtacgt ggccatgtac tacccgtccg accaagccgt gcagggcgac   3240
acggagctgc agtcgtggta cagggaggcg gtgcagacgg ggcacgcgga caagcgcggc   3300
gcgccgtggt ggccgcgcct gtcgacgccg gcgacctgg cgtcgctgct caccacgctg   3360
ctgtggctca cctcggcgca gcacgcggcg ctcaacttcg ggcagtaccc gctgggcggc   3420
tacatcccga accgaccgcc gctcatgcgg cggctggtgc cgccgacgg cgacccggag   3480 tacgcgcacc tggtggccga cccgcaccgc ttcttcctgt cggcgctgcc cagcctgacg   3540
cagacgacca ccttcatgac cgtcatcgac acgctgtcca cgcactccgc cgacgagcag   3600
tacctcgggg agcggcccga cgaggcgtgg acggccgacc cggcggcgct ggcggcggcg   3660
cgcgagttcg cggacgaggt gcgccgcgcc gaggaggaga tcgaccggcg caacgcggac   3720
acgggacgcc gcaaccggtg cggcgccggc gtgctgccgt acgagctcat ggcgcccacg   3780
tccgggccgg gcatcacctg ccgcggcatc cccaacagcg tcaccattta gtctctcgcg   3840
gtaccgatag ccatgggaga aatctaagca gaagcaaaat gattttttt ttgctttact    3900 tctcccccat tgccaaattg ccattgattt ggaggtctga acaggtggag tttgatttt    3960 gactagggga gagacactga ggaactgaat gggtgtaaat aatttgttat tatagaaaaa   4020
aaatcaatga aatataatca ttagagtt                                      4048
```

<210> SEQ ID NO 5
<211> LENGTH: 401
<212> TYPE: PRT
<213> ORGANISM: Sorghum bicolor

```
<400> SEQUENCE: 5

Met Ala Ser Ala Met Glu Leu Val Gly Arg Ser Phe Leu Pro Gly Ser
1               5                   10                  15

Ala Ala Ala Ala Ser Pro Ala Gly Arg Glu Arg Arg Gly Gly Pro
            20                  25                  30

Cys Phe Ala Ala Val Gly Arg Glu Gly Ser Ala His Lys Arg Arg Pro
            35                  40                  45

Ser Leu Arg Ser Thr Ala Pro Val Gly Ala Leu Ala Glu Arg Val Val
        50                  55                  60

Val Thr Pro Ala Pro Glu Glu Arg Ala Gly Thr Ala Pro Pro Glu
65                  70                  75                  80

Pro His Pro Gln Ser Val Ala Ala Arg Ala Val Val Thr Val Arg Arg
                85                  90                  95

Arg Arg Lys Glu Asp Ala Lys Arg Arg Val Ala Glu Gln Leu Asp Ala
            100                 105                 110

Tyr Ala Asp Arg Val Gly Arg Ser Val Leu Leu Glu Leu Ile Ser Thr
            115                 120                 125

Glu Thr Asp Pro Arg Lys Gly Gly Pro Lys Lys Ser Arg Arg Ser Ala
130                 135                 140

Leu Val Gly Trp Phe Glu Lys Lys Asp Val Lys Ala Glu Arg Val Val
145                 150                 155                 160

Tyr Thr Ala Asp Phe Thr Val Asp Gly Cys Phe Gly Pro Gly Ala
            165                 170                 175

Val Thr Val Leu Asn Arg His Gln Arg Glu Phe Phe Ile Glu Ser Ile
            180                 185                 190

Val Val Glu Gly Phe Pro Ser Gly Pro Ala His Phe Thr Cys Asn Ser
            195                 200                 205

Trp Val Gln Pro Thr Arg Val Asp Arg Asn Pro Arg Val Phe Phe Thr
            210                 215                 220

Asn Lys Pro Tyr Leu Pro Ala Glu Thr Pro Pro Gly Leu Gln Glu Leu
225                 230                 235                 240

Arg Arg Gln Glu Leu Ser Asp Leu Arg Gly Glu Gly Ala Asp Thr
            245                 250                 255

Thr Gly Glu Arg Arg Ile Thr Asp Arg Val Trp Glu Tyr Asp Val Tyr
            260                 265                 270

Asn Asp Leu Gly Asn Pro Asp Lys Gly Ala Glu Phe Ala Arg Pro Ile
            275                 280                 285

Leu Gly Gly Glu Gln Gln Leu Pro Tyr Pro Arg Arg Met Arg Thr Gly
            290                 295                 300

Arg Pro Lys Thr Phe Thr Asp Arg Ala Glu Ser Arg Val Glu Tyr
305                 310                 315                 320

Pro Glu Pro Ile Tyr Val Ser Arg Asp Glu Glu Phe Glu Glu Gly Lys
            325                 330                 335

Asn Glu Met Leu Ser Glu Gly Ala Leu Lys Ala Leu His Asn Phe
            340                 345                 350

Met Pro Leu Leu Val Ser Ser Val Ser Pro Asp Ile Arg Asp Phe Ala
            355                 360                 365

Gly Phe His Asp Val Asp Asn Leu Phe Lys Glu Gly Leu Arg Leu Lys
            370                 375                 380

Gln Ala Leu Gln Asp Gln Leu Phe Gln Lys Ile Pro Phe Val Arg Lys
385                 390                 395                 400

Ile
```

<210> SEQ ID NO 6
<211> LENGTH: 1206
<212> TYPE: DNA
<213> ORGANISM: Sorghum bicolor

<400> SEQUENCE: 6

| | | |
|---|---|---|
| atggcgtcgg cgatggagct ggttgggaga tctttcttgc cgggctctgc cgccgcggcg | 60 |
| tcgccggcgg gccgggagcg gcggcgaggc gggccctgct tcgccgcggt cggaagggag | 120 |
| gggagtgcgc acaagcggcg gccgtcgctg aggtcgaccg cgccggtggg cgcgctggcc | 180 |
| gagcgcgtcg tggtgacccc ggcgccgccg aggagaggg ccgggacggc cccgccggag | 240 |
| ccgcacccgc agagcgtggc cgcgcgcgcc gtggtcaccg tgcggcggag cgcaaggag | 300 |
| gacgccaagc gccgcgtcgc cgagcagctg acgcctacg ccgacagggt cggccgcagc | 360 |
| gtcctcctcg agctcatcag cacggagacc gacccaagaa aaggggggccc caagaagagc | 420 |
| cggcggtcgg cgctggtggg gtggttcgag aagaaggacg tcaaggcgga gcgggtggtg | 480 |
| tacacggcgg acttcaccgt cgacgggtgc ttcggcgagc ctggcgccgt caccgtgctc | 540 |
| aaccggcacc agcgcgagtt cttcatcgag agcatcgtgg tggagggctt ccctcgggc | 600 |
| cccgcgcact tcacctgcaa ctcgtgggtg cagcccaccc gcgtggaccg caacccgcgc | 660 |
| gtgttcttca ccaacaagcc ctacctgccg gccgagacgc cgccggggct gcaggagctc | 720 |
| cgccgccagg agctcagcga cctgagggggc gagggcggcg ccgacaccac cggcgagcgc | 780 |
| aggatcaccg accgggtgtg ggagtacgac gtgtacaacg acctcggcaa cccggacaag | 840 |
| ggcgccgagt tcgcgcgccc gatcctcggc ggcgagcagc agctgccgta cccgcgccgg | 900 |
| atgcgaacgg gccggcccaa gaccttcaca gacgatcgcg cggagagcag ggtggagtac | 960 |
| ccggagccca tctacgtgtc ccgggacgag gagttcgagg agggcaagaa cgagatgctg | 1020 |
| tcggagggcg cgctcaaggc gctgctccac aacttcatgc cgctgctggt gagctccgtg | 1080 |
| tcgccggaca tccgcgactt cgccggcttc cacgacgtgg acaacctctt caaggagggc | 1140 |
| ctccggctga agcaggcact gcaggaccag ctgttccaga gatccccctt cgtgcgcaag | 1200 |
| atctag | 1206 |

<210> SEQ ID NO 7
<211> LENGTH: 4048
<212> TYPE: DNA
<213> ORGANISM: Sorghum bicolor

<400> SEQUENCE: 7

| | | |
|---|---|---|
| atggcgtcgg cgatggagct ggttgggaga tctttcttgc cgggctctgc cgccgcggcg | 60 |
| tcgccggcgg gccgggagcg gcggcgaggc gggccctgct tcgccgcggt cggaagggag | 120 |
| gggagtgcgc acaagcggcg gccgtcgctg aggtcgaccg cgccggtggg cgcgctggcc | 180 |
| gagcgcgtcg tggtgacccc ggcgccgccg aggagaggg ccgggacggc cccgccggag | 240 |
| ccgcacccgc agagcgtggc cgcgcgcgcc gtggtcaccg tgcggcggag cgcaaggag | 300 |
| gacgccaagc gccgcgtcgc cgagcagctg acgcctacg ccgacagggt cggccgcagc | 360 |
| gtcctcctcg agctcatcag cacggagacc gacccaagta agaaacattt cttccgtgat | 420 |
| cccacctcca ccacccccac cgccgccgcc gccgcgcgc gacggcatgg aattccatgg | 480 |
| cgcatccggc gggcggttgc gttgcatctt tgaattgtat gctactagca gtagcacaat | 540 |
| ttggttccat tttcttctct cctcctcgcc cttttttcca ttccactcgc cgctccttca | 600 |

```
ccttcatgga aacccgcgcg cggcgagaat attccagctg gtgcgccttg acgtctgggg      660
cctctgtctc cgagtcatca tctccaaatg gaccatcacg tggagctgtc tctcttgatt      720
tgatttctgc caaaagccgc cgtctttacc gtctcctcgg cgtcgaaacg gaaatggaac      780
gaattttact tacgcctggc ggcgagcatt cacctgacga tcgaaatgaa ttggtggcag      840
gaaaaggggg ccccaagaag agccggcggt cggcgctggt ggggtggttc gagaagaagg      900
acgtcaaggc ggagcgggtg gtgtacacgg cggacttcac cgtcgacggg tgcttcggcg      960
agcctggcgc cgtcaccgtg ctcaaccggc accagcgcga gttcttcatc gagagcatcg     1020
tggtggaggc ctttccctcg ggcccgcgc acttcacctg caactcgtgg gtgcagccca      1080
cccgcgtgga ccgcaacccg cgcgtgttct tcaccaacaa gccctacctg ccggccgaga     1140
cgccgccggg gctgcaggag ctccgccgcc aggagctcag cgacctgagg ggcgagggcg     1200
gcgccgacac caccggcgag cgcaggatca ccgaccgggt gtgggagtac gacgtgtaca     1260
acgacctcgg caacccggac aagggcgccg agttcgcgcg cccgatcctc ggcggcgagc     1320
agcagctgcc gtacccgcgc cggatgcgaa cgggccggcc caagaccttc acaggtgcag     1380
cctccctctc cgctttcaat tcccctctca ctcttcactt cttgtcacca ccgccgtccg     1440
ccccataaat cccgcgacag taactgtggc cgaccggaca cggcggaggt cgccgtcgcg     1500
cgtagctttc gtatcgaaac cacccgatcg cgggcgacgt tgaccgaccg acgctaacat     1560
ttcgtcacgc acgcacggtg cttgctgctt tgcttgctcg ctcgcagacg atcgcgcgga     1620
gagcagggtg gagtacccgg agcccatcta cgtgtcccgg gacgaggagt cgaggaggg     1680 caagaacgag atgctgtcgg agggcgcgct caaggcgctg ctccacaact tcatgccgct     1740
gctggtgagc tccgtgtcgc cggacatccg cgacttcgcc ggcttccacg acgtggacaa     1800
cctcttcaag gagggcctcc ggctgaagca ggcactgcag gaccagctgt tccagaagat     1860 cccccttcgtg cgcaagatcc aggagaacag cgagggcctc ctccgctacg cacgcccga     1920 catcatcaag agtaagcgac ccccacccat gatccatgga gattcgatac gataagatac     1980
ggggcacgac aatggtgtgc tcatgctgtc attctgtgtg gcagaggaca agtttgtgtg     2040
gctgcgcgac gacgagttcg cgaggcaggc gctggctggc atcaaccccg tcaacatcga     2100
gcggcttcag gtacacattt caatcacaag cccaacacgc cgcggacatt gagactacac     2160
gtccactgct cgctcatctc actgccgttc gtttcctcgt gtctctcttc ccaggcgttc     2220
ccgccgatga gcaagctgga cccggccgtg tacggcccgc cggagtcggc catcacggag     2280
gagcacatca tcgggcagct ggacggcatg tcggtgcggc aggcgctgca ggacaaccgg     2340
ctgtacatgc tggactacca cgacatcttc ctgccgttcc tggaccggat caacgcgcag     2400
gacgggcgga aggcctacgg cacgcgcacg ctcttcttcc tgacggcggc gggcacgctc     2460
aagcccatcg ccatcgagct gtgcctgccg cccatgaccg acgggtgcgc gcgcgccaag     2520
cgggtgttca cgccgcccgc cgacgccacc agcaactggc tgtggcagct cgccaaggcg     2580
cacgtctgct ccaacgacgc cggcgtccac cagctcatca accactggta cgacacgaca     2640
ctgtctgtgt cagtcttgca ggaggaggca atctcaaagt caaaagtgtt ggattccact     2700
gatcatgagt tgtgccaggc tgaggacgca cgcgtgcatg gagccgttca tcatctcggc     2760
gcaccggcag ctgagcgcga tgcaccccat cttcaagctg ctcaagccgc acatgcgcta     2820
cacgctcaag atcaacgcgc tggcgcggca gatcctcatc aacggcgacg gcgtcatcga     2880
gtccggcttc acccccggcc gctactgcat ggagatgagc tcgttcgcgt accaggagct     2940
ctggcggctc gaccaggagg gcctccctgc cgatctcatc agaaggtaca cagatcaatc     3000
```

```
aatcacatga aagttgtgat gcttcgtgcg atgcaatggt gcttgctgac atgggtgttt    3060
tctttgtcac aacacagagg aatggccgtg gaggacccga cgcagccgca cggtctccgg    3120
ctgctgatcg aggactaccc gtacgccacc gacgggctgc tcctctggga cgccatcacg    3180
cggtggtgcg acgcgtacgt ggccatgtac tacccgtccg accaagccgt gcagggcgac    3240
acggagctgc agtcgtggta cagggaggcg gtgcagacgg ggcacgcgga caagcgcggc    3300
gcgccgtggt ggccgcgcct gtcgacgccg gcgacctggc cgtcgctgct caccacgctg    3360
ctgtggctca cctcggcgca gcacgcggcg ctcaacttcg ggcagtaccc gctgggcggc    3420
tacatcccga accgaccgcc gctcatgcgg cggctggtgc cgccgacgg cgacccggag    3480 tacgcgcacc tggtggccga cccgcaccgc ttcttcctgt cggcgctgcc cagcctgacg    3540
cagacgacca ccttcatgac cgtcatcgac acgctgtcca cgcactccgc cgacgagcag    3600
tacctcgggg agcggcccga cgaggcgtgg acggccgacc cggcggcgct ggcggcggcg    3660
cgcgagttcg cggacgaggt gcgccgcgcc gaggaggaga tcgaccggcg caacgcggac    3720
acgggacgcc gcaaccggtg cggcgccggc gtgctgccgt acgagctcat ggcgcccacg    3780
tccgggccgg gcatcacctg ccgcggcatc cccaacagcg tcaccattta gtctctcgcg    3840
gtaccgatag ccatgggaga atctaagca gaagcaaaat gattttttt ttgctttact    3900 tctccccat tgccaaattg ccattgattt ggaggtctga acaggtggag tttgattttt    3960
gactagggga gagacactga ggaactgaat gggtgtaaat aatttgttat tatagaaaaa    4020
aaatcaatga aatataatca ttagagtt                                      4048
```

<210> SEQ ID NO 8
<211> LENGTH: 924
<212> TYPE: PRT
<213> ORGANISM: Sorghum bicolor

<400> SEQUENCE: 8

Met Ala Ser Ala Met Glu Leu Val Gly Arg Ser Phe Leu Pro Gly Ser
1               5                   10                  15

Ala Ala Ala Ser Pro Ala Gly Arg Glu Arg Arg Gly Gly Pro
            20                  25                  30

Cys Phe Ala Ala Val Gly Arg Glu Gly Ser Ala His Lys Arg Arg Pro
        35                  40                  45

Ser Leu Arg Ser Thr Ala Pro Val Gly Ala Leu Ala Glu Arg Val Val
    50                  55                  60

Val Thr Pro Ala Pro Glu Glu Arg Ala Gly Thr Ala Pro Glu
65                  70                  75                  80

Pro His Pro Gln Ser Val Ala Ala Arg Ala Val Thr Val Arg Arg
                85                  90                  95

Arg Arg Lys Glu Asp Ala Lys Arg Arg Val Ala Glu Gln Leu Asp Ala
            100                 105                 110

Tyr Ala Asp Arg Val Gly Arg Ser Val Leu Leu Glu Leu Ile Ser Thr
        115                 120                 125

Glu Thr Asp Pro Arg Lys Gly Gly Pro Lys Lys Ser Arg Arg Ser Ala
    130                 135                 140

Leu Val Gly Trp Phe Glu Lys Lys Asp Val Lys Ala Glu Arg Val Val
145                 150                 155                 160

Tyr Thr Ala Asp Phe Thr Val Asp Gly Cys Phe Gly Glu Pro Gly Ala
                165                 170                 175

Val Thr Val Leu Asn Arg His Gln Arg Glu Phe Phe Ile Glu Ser Ile

-continued

```
                180             185             190
Val Val Glu Gly Phe Pro Ser Gly Pro Ala His Phe Thr Cys Asn Ser
            195                 200                 205
Trp Val Gln Pro Thr Arg Val Asp Arg Asn Pro Arg Val Phe Phe Thr
210                 215                 220
Asn Lys Pro Tyr Leu Pro Ala Glu Thr Pro Pro Gly Leu Gln Glu Leu
225                 230                 235                 240
Arg Arg Gln Glu Leu Ser Asp Leu Arg Gly Glu Gly Ala Asp Thr
            245                 250                 255
Thr Gly Glu Arg Arg Ile Thr Asp Arg Val Trp Glu Tyr Asp Val Tyr
            260                 265                 270
Asn Asp Leu Gly Asn Pro Asp Lys Gly Ala Glu Phe Ala Arg Pro Ile
            275                 280                 285
Leu Gly Gly Glu Gln Gln Leu Pro Tyr Pro Arg Met Arg Thr Gly
            290                 295                 300
Arg Pro Lys Thr Phe Thr Asp Arg Ala Glu Ser Arg Val Glu Tyr
305                 310                 315                 320
Pro Glu Pro Ile Tyr Val Ser Arg Asp Glu Glu Phe Glu Glu Gly Lys
                325                 330                 335
Asn Glu Met Leu Ser Glu Gly Ala Leu Lys Ala Leu Leu His Asn Phe
            340                 345                 350
Met Pro Leu Leu Val Ser Ser Val Ser Pro Asp Ile Arg Asp Phe Ala
            355                 360                 365
Gly Phe His Asp Val Asp Asn Leu Phe Lys Glu Gly Leu Arg Leu Lys
        370                 375                 380
Gln Ala Leu Gln Asp Gln Leu Phe Gln Lys Ile Pro Phe Val Arg Lys
385                 390                 395                 400
Ile Gln Glu Asn Ser Glu Gly Leu Leu Arg Tyr Asp Thr Pro Asp Ile
                405                 410                 415
Ile Lys Lys Asp Lys Phe Val Trp Leu Arg Asp Asp Glu Phe Ala Arg
                420                 425                 430
Gln Ala Leu Ala Gly Ile Asn Pro Val Asn Ile Glu Arg Leu Gln Ala
            435                 440                 445
Phe Pro Pro Met Ser Lys Leu Asp Pro Ala Val Tyr Gly Pro Pro Glu
            450                 455                 460
Ser Ala Ile Thr Glu Glu His Ile Ile Gly Gln Leu Asp Gly Met Ser
465                 470                 475                 480
Val Arg Gln Ala Leu Gln Asp Asn Arg Leu Tyr Met Leu Asp Tyr His
                485                 490                 495
Asp Ile Phe Leu Pro Phe Leu Asp Arg Ile Asn Ala Gln Asp Gly Arg
            500                 505                 510
Lys Ala Tyr Gly Thr Arg Thr Leu Phe Phe Leu Thr Ala Ala Gly Thr
            515                 520                 525
Leu Lys Pro Ile Ala Ile Glu Leu Cys Leu Pro Pro Met Thr Asp Gly
            530                 535                 540
Cys Ala Arg Ala Lys Arg Val Phe Thr Pro Pro Ala Asp Ala Thr Ser
545                 550                 555                 560
Asn Trp Leu Trp Gln Leu Ala Lys Ala His Val Cys Ser Asn Asp Ala
                565                 570                 575
Gly Val His Gln Leu Ile Asn His Trp Leu Arg Thr His Ala Cys Met
            580                 585                 590
Glu Pro Phe Ile Ile Ser Ala His Arg Gln Leu Ser Ala Met His Pro
            595                 600                 605
```

```
Ile Phe Lys Leu Leu Lys Pro His Met Arg Tyr Thr Leu Lys Ile Asn
        610                 615                 620

Ala Leu Ala Arg Gln Ile Leu Ile Asn Gly Asp Gly Val Ile Glu Ser
625                 630                 635                 640

Gly Phe Thr Pro Gly Arg Tyr Cys Met Glu Met Ser Ser Phe Ala Tyr
            645                 650                 655

Gln Glu Leu Trp Arg Leu Asp Gln Glu Gly Leu Pro Ala Asp Leu Ile
        660                 665                 670

Arg Arg Gly Met Ala Val Glu Asp Pro Thr Gln Pro His Gly Leu Arg
    675                 680                 685

Leu Leu Ile Glu Asp Tyr Pro Tyr Ala Thr Asp Gly Leu Leu Leu Trp
690                 695                 700

Asp Ala Ile Thr Arg Trp Cys Asp Ala Tyr Val Ala Met Tyr Tyr Pro
705                 710                 715                 720

Ser Asp Gln Ala Val Gln Gly Asp Thr Glu Leu Gln Ser Trp Tyr Arg
            725                 730                 735

Glu Ala Val Gln Thr Gly His Ala Asp Lys Arg Gly Ala Pro Trp Trp
        740                 745                 750

Pro Arg Leu Ser Thr Pro Gly Asp Leu Ala Ser Leu Leu Thr Thr Leu
    755                 760                 765

Leu Trp Leu Thr Ser Ala Gln His Ala Ala Leu Asn Phe Gly Gln Tyr
770                 775                 780

Pro Leu Gly Gly Tyr Ile Pro Asn Arg Pro Pro Leu Met Arg Arg Leu
785                 790                 795                 800

Val Pro Ala Asp Gly Asp Pro Glu Tyr Ala His Leu Val Ala Asp Pro
            805                 810                 815

His Arg Phe Phe Leu Ser Ala Leu Pro Ser Leu Thr Gln Thr Thr Thr
        820                 825                 830

Phe Met Thr Val Ile Asp Thr Leu Ser Thr His Ser Ala Asp Glu Gln
    835                 840                 845

Tyr Leu Gly Glu Arg Pro Asp Glu Ala Trp Thr Ala Asp Pro Ala Ala
850                 855                 860

Leu Ala Ala Ala Arg Glu Phe Ala Asp Glu Val Arg Arg Ala Glu Glu
865                 870                 875                 880

Glu Ile Asp Arg Arg Asn Ala Asp Thr Gly Arg Arg Asn Arg Cys Gly
            885                 890                 895

Ala Gly Val Leu Pro Tyr Glu Leu Met Ala Pro Thr Ser Gly Pro Gly
        900                 905                 910

Ile Thr Cys Arg Gly Ile Pro Asn Ser Val Thr Ile
    915                 920

<210> SEQ ID NO 9
<211> LENGTH: 2774
<212> TYPE: DNA
<213> ORGANISM: Sorghum bicolor

<400> SEQUENCE: 9
atggcgtcgg cgatggagct ggttgggaga tctttcttgc cgggctctgc cgccgcggcg      60
tcgccggcgg ccgggagcg gcggcgaggc gggccctgct tcgccgcggt cggaagggag     120
gggagtgcgc acaagcggcg gccgtcgctg aggtcgaccg cgccggtggg cgcgctggcc     180
gagcgcgtcg tggtgacccc ggcgccgccg aggagaggg ccgggacggc cccgccggag     240
ccgcacccgc agagcgtggc cgcgcgcgcc gtggtcaccg tgcggcggag gcgcaaggag     300
```

-continued

```
gacgccaagc gccgcgtcgc cgagcagctg gacgcctacg ccgacagggt cggccgcagc      360
gtcctcctcg agctcatcag cacggagacc gacccaagaa aagggggccc caagaagagc      420
cggcggtcgg cgctggtggg gtggttcgag aagaaggacg tcaaggcgga gcgggtggtg      480
tacacggcgg acttcaccgt cgacgggtgc ttcggcgagc ctggcgccgt caccgtgctc      540
aaccggcacc agcgcgagtt cttcatcgag agcatcgtgg tggagggctt ccctcgggc       600 cccgcgcact tcacctgcaa ctcgtgggtg cagcccaccc gcgtggaccg caacccgcgc      660
gtgttcttca ccaacaagcc ctacctgccg gccgagacgc cgccggggct gcaggagctc      720
cgccgccagg agctcagcga cctgaggggc gagggcggcg ccgacaccac cggcgagcgc      780
aggatcaccg accgggtgtg ggagtacgac gtgtacaacg acctcggcaa cccggacaag      840
ggcgccgagt tcgcgcgccc gatcctcggc ggcgagcagc agctgccgta cccgcgccgg      900
atgcgaacgg gccggcccaa gaccttcaca gacgatcgcg cggagagcag ggtggagtac      960
ccggagccca tctacgtgtc ccgggacgag gagttcgagg agggcaagaa cgagatgctg     1020
tcggagggcg cgctcaaggc gctgctccac aacttcatgc cgctgctggt gagctccgtg     1080
tcgccggaca tccgcgactt cgccggcttc cacgacgtgg acaacctctt caaggagggc     1140
ctccggctga agcaggcact gcaggaccag ctgttccaga agatcccctt cgtgcgcaag     1200
atccaggaga acagcgaggg cctcctccgc tacgacacgc ccgacatcat caagaaggac     1260
aagtttgtgt ggctgcgcga cgacgagttc gcgaggcagg cgctggctgg catcaacccc     1320
gtcaacatcg agcggcttca ggcgttcccg ccgatgagca agctggaccc ggccgtgtac     1380
ggcccgccgg agtcggccat cacggaggag cacatcatcg ggcagctgga cggcatgtcg     1440
gtgcggcagg cgctgcagga caaccggctg tacatgctgg actaccacga catcttcctg     1500
ccgttcctgg accggatcaa cgcgcaggac gggcggaagg cctacggcac gcgcacgctc     1560
ttcttcctga cggcggcggg cacgctcaag cccatcgcca tcgagctgtg cctgccgccc     1620
atgaccgacg ggtgcgcgcg cgccaagcgg gtgttcacgc cgcccgccga cgccaccagc     1680
aactggctgt ggcagctcgc caaggcgcac gtctgctcca cgacgccgg cgtccaccag     1740 ctcatcaacc actggctgag gacgcacgcg tgcatggagc cgttcatcat ctcggcgcac     1800
cggcagctga gcgcgatgca ccccatcttc aagctgctca agccgcacat gcgctacacg     1860
ctcaagatca cgcgctggc gcggcagatc ctcatcaacg cgacggcgt catcgagtcc       1920 ggcttcaccc ccggccgcta ctgcatggag atgagctcgt tcgcgtacca ggagctctgg     1980
cggctcgacc aggagggcct ccctgccgat ctcatcagaa gaggaatggc cgtggaggac     2040
ccgacgcagc cgcacggtct ccggctgctg atcgaggact acccgtacgc caccgacggg     2100
ctgctcctct gggacgccat cacgcggtgg tgcgacgcgt acgtggccat gtactacccg     2160
tccgaccaag ccgtgcaggg cgacacggag ctgcagtcgt ggtacaggga ggcggtgcag     2220
acggggcacg cggacaagcg cggcgcgccg tggtggccgc gcctgtcgac gccgggcgac     2280
ctggcgtcgc tgctcaccac gctgctgtgg ctcacctcgg cgcagcacgc ggcgctcaac     2340
ttcgggcagt acccgctggg cggctacatc ccgaaccgac gccgctcat gcggcggctg     2400 gtgcccgccg acgcgacccc ggagtacgcg cacctggtgg ccgacccgca ccgcttcttc     2460
ctgtcggcgc tgcccagcct gacgcagacg accaccttca tgaccgtcat cgacacgctg     2520
tccacgcact ccgccgacga gcagtacctc ggggagcggc ccgacgaggc gtggacggcc     2580
gacccggcgg cgctgcgcgc ggcgcgcgag ttcgcggacg aggtgcgccg cgccgaggag     2640
gagatcgacc ggcgcaacgc ggacacggga cgccgcaacc ggtgcggcgc cggcgtgctg     2700
```

```
ccgtacgagc tcatggcgcc cacgtccggg ccgggcatca cctgccgcgg catccccaac    2760
agcgtcacca ttta                                                       2774

<210> SEQ ID NO 10
<211> LENGTH: 4048
<212> TYPE: DNA
<213> ORGANISM: Sorghum bicolor

<400> SEQUENCE: 10
atggcgtcgg cgatggagct ggttgggaga tctttcttgc cgggctctgc cgccgcggcg     60
tcgccggcgg gccgggagcg gcggcgaggc gggccctgct tcgccgcggt cggaagggag    120
gggagtgcgc acaagcggcg gccgtcgctg aggtcgaccg cgccggtggg cgcgctggcc    180
gagcgcgtcg tggtgacccc ggccgccgcc gaggagaggg ccgggacggc cccgccggag    240
ccgcacccgc agagcgtggc cgcgcgcgcc gtggtcaccg tgcggcggag cgcaaggag     300 gacgccaagc gccgcgtcgc cgagcagctg acgcctacg ccgacagggt cggccgcagc    360
gtcctcctcg agctcatcag cacggagacc gacccaagta agaaacattt cttccgtgat    420
cccacctcca ccaccccac cgccgccgcc gccgcgcgc gacggcatgg aattccatgg     480
cgcatccggc gggcggttgc gttgcatctt tgaattgtat gctactagca gtagcacaat    540
ttggttccat tttcttctct cctcctcgcc cttttttcca ttccactcgc cgctccttca    600
ccttcatgga aacccgcgcg cggcgagaat attccagctg gtgcgccttg acgtctgggg    660
cctctgtctc cgagtcatca tctccaaatg gaccatcacg tggagctgtc tctcttgatt    720
tgatttctgc caaaagccgc cgtctttacc gtctcctcgg cgtcgaaacg gaaatggaac    780
gaattttact tacgcctggc ggcgagcatt cacctgacga tcgaaatgaa ttggtggcag    840 gaaaagggg ccccaagaag agccggcggt cggcgctggt ggggtggttc gagaagaagg    900
acgtcaaggc ggagcgggtg gtgtacacg cggacttcac cgtcgacggg tgcttcggcg    960
agcctggcgc cgtcaccgtg ctcaaccggc accagcgcga gttcttcatc gagagcatcg   1020
tggtggaggg cttcccctcg ggccccgcgc acttcacctg caactcgtgg gtgcagccca   1080
cccgcgtgga ccgcaacccg cgcgtgttct tcaccaacaa gccctacctg ccggccgaga   1140
cgccgccggg gctgcaggag ctccgccgcc aggagctcag cgacctgagg ggcgagggcg   1200
gcgccgacac caccggcgag cgcaggatca ccgaccgggt gtgggagtac gacgtgtaca   1260
acgacctcgg caacccggac aagggcgccg agttcgcgcg cccgatcctc ggcggcgagc   1320
agcagctgcc gtaccgcgc cggatgcgaa cgggccggcc caagaccttc acaggtgcag   1380
cctccctctc cgctttcaat tcccctctca ctcttcactt cttgtcacca ccgccgtccg   1440
ccccataaat cccgcgacag taactgtggc cgaccggaca cggcggaggt cgccgtcgcg   1500
cgtagctttc gtatcgaaac cacccgatcg cgggcgacgt tgaccgaccg acgctaacat   1560
ttcgtcacgc acgcacggtg cttgctgctt tgcttgctcg ctcgcagacg atcgcgcgga   1620
gagcagggtg gagtacccgg agcccatcta cgtgtcccgg gacgaggagt cgaggaggg    1680 caagaacgag atgctgtcgg agggcgcgct caaggcgctg ctccacaact tcatgccgct   1740
gctggtgagc tccgtgtcgc cggacatccg cgacttcgcc ggcttccacg acgtggacaa   1800
cctcttcaag gagggcctcc ggctgaagca ggcactgcag gaccagctgt tccagaagat   1860 cccccttcgtg cgcaagatct aggagaacag cgagggcctc ctccgctacg acacgcccga   1920
catcatcaag agtaagcgac ccccacccat gatccatgga gattcgatac gataagatac   1980
```

| | | | | |
|---|---|---|---|---|
| ggggcacgac | aatggtgtgc | tcatgctgtc | attctgtgtg | gcagaggaca | agtttgcgtg | 2040 |
| gctgcgcgac | gacgagttcg | cgaggcaggc | gctggctggc | atcaaccccg | tcaacatcga | 2100 |
| gcggcttcag | gtacacattt | caatcacaag | cccaacacgc | cgcggacatt | gagactacac | 2160 |
| gtccactgct | cgctcatctc | actgccgttc | gtttcctcgt | gtctctcttc | ccaggcgttc | 2220 |
| ccgccgatga | gcaagctgga | cccggccgtg | tacggcccgc | cggagtcggc | catcacggag | 2280 |
| gagcacatca | tcgggcagct | ggacggcatg | tcggtgcggc | aggcgctgca | ggacaaccgg | 2340 |
| ctgtacatgc | tggactacca | cgacatcttc | ctgccgttcc | tggaccggat | caacgcgcag | 2400 |
| gacgggcgga | aggcctacgg | cacgcgcacg | ctcttcttcc | tgacggcggc | gggcacgctc | 2460 |
| aagcccatcg | ccatcgagct | gtgcctgccg | cccatgaccg | acgggtgcgc | gcgcgccaag | 2520 |
| cgggtgttca | cgccgcccgc | cgacgccacc | agcaactggc | tgtggcagct | cgccaaggcg | 2580 |
| cacgtctgct | ccaacgacgc | cggcgtccac | cagctcatca | accactggta | cgacacgaca | 2640 |
| ctgtctgtgt | cagtcttgca | ggaggaggca | atctcaaagt | caaaagtgtt | ggattccact | 2700 |
| gatcatgagt | tgtgccaggc | tgaggacgca | cgcgtgcatg | gagccgttca | tcatctcggc | 2760 |
| gcaccggcag | ctgagcgcga | tgcaccccat | cttcaagctg | ctcaagccgc | acatgcgcta | 2820 |
| cacgctcaag | atcaacgcgc | tggcgcggca | gatcctcatc | aacggcgacg | gcgtcatcga | 2880 |
| gtccggcttc | accccggcc | gctactgcat | ggagatgagc | tcgttcgcgt | accaggagct | 2940 |
| ctggcggctc | gaccaggagg | gcctccctgc | cgatctcatc | agaaggtaca | cagatcaatc | 3000 |
| aatcacatga | agttgtgat | gcttcgtgcg | atgcaatggt | gcttgctgac | atgggtgttt | 3060 |
| tctttgtcac | aacacagagg | aatggccgtg | gaggacccga | cgcagccgca | cggtctccgg | 3120 |
| ctgctgatcg | aggactaccc | gtacgccacc | gacgggctgc | tcctctggga | cgccatcacg | 3180 |
| cggtggtgcg | acgcgtacgt | ggccatgtac | tacccgtccg | accaagccgt | gcagggcgac | 3240 |
| acggagctgc | agtcgtggta | cagggaggcg | gtgcagacgg | ggcacgcgga | caagcgcggc | 3300 |
| gcgccgtggt | ggccgcgcct | gtcgacgccg | ggcgacctgg | cgtcgctgct | caccacgctg | 3360 |
| ctgtggctca | cctcggcgca | gcacgcggcg | ctcaacttcg | ggcagtaccc | gctgggcggc | 3420 |
| tacatcccga | accgaccgcc | gctcatgcgg | cggctggtgc | cgccgacgg | cgacccggag | 3480 |
| tacgcgcacc | tggtggccga | cccgcaccgc | ttcttcctgt | cggcgctgcc | cagcctgacg | 3540 |
| cagacgacca | ccttcatgac | cgtcatcgac | acgctgtcca | cgcactccgc | cgacgagcag | 3600 |
| tacctcgggg | agcggcccga | cgaggcgtgg | acggccgacc | cggcggcgct | ggcggcggcg | 3660 |
| cgcgagttcg | cggacgaggt | gcgccgcgcc | gaggaggaga | tcgaccggcg | caacgcggac | 3720 |
| acgggacgcc | gcaaccggtg | cggcgccggc | gtgctgccgt | acgagctcat | ggcgcccacg | 3780 |
| tccgggccgg | gcatcacctg | ccgcggcatc | cccaacagcg | tcaccattta | gtctctcgcg | 3840 |
| gtaccgatag | ccatgggaga | aatctaagca | gaagcaaaat | gatttttttt | ttgctttact | 3900 |
| tctcccccat | tgccaaattg | ccattgattt | ggaggtctga | acaggtggag | tttgatttt | 3960 |
| gactagggga | gagacactga | ggaactgaat | gggtgtaaat | aatttgttat | tatagaaaaa | 4020 |
| aaatcaatga | aatataatca | ttagagtt | | | | 4048 |

<210> SEQ ID NO 11
<211> LENGTH: 401
<212> TYPE: PRT
<213> ORGANISM: Sorghum bicolor

<400> SEQUENCE: 11

Met Ala Ser Ala Met Glu Leu Val Gly Arg Ser Phe Leu Pro Gly Ser

```
  1               5                   10                  15
Ala Ala Ala Ala Ser Pro Ala Gly Arg Glu Arg Arg Gly Gly Pro
                20                  25                  30
Cys Phe Ala Ala Val Gly Arg Glu Gly Ser Ala His Lys Arg Arg Pro
                35                  40                  45
Ser Leu Arg Ser Thr Ala Pro Val Gly Ala Leu Ala Glu Arg Val Val
 50                  55                  60
Val Thr Pro Ala Pro Glu Glu Arg Ala Gly Thr Ala Pro Pro Glu
 65                  70                  75                  80
Pro His Pro Gln Ser Val Ala Ala Arg Ala Val Val Thr Val Arg Arg
                85                  90                  95
Arg Arg Lys Glu Asp Ala Lys Arg Arg Val Ala Glu Gln Leu Asp Ala
                100                 105                 110
Tyr Ala Asp Arg Val Gly Arg Ser Val Leu Leu Glu Leu Ile Ser Thr
                115                 120                 125
Glu Thr Asp Pro Arg Lys Gly Gly Pro Lys Lys Ser Arg Arg Ser Ala
                130                 135                 140
Leu Val Gly Trp Phe Glu Lys Lys Asp Val Lys Ala Glu Arg Val Val
145                 150                 155                 160
Tyr Thr Ala Asp Phe Thr Val Asp Gly Cys Phe Gly Pro Gly Ala
                165                 170                 175
Val Thr Val Leu Asn Arg His Gln Arg Glu Phe Phe Ile Glu Ser Ile
                180                 185                 190
Val Val Glu Gly Phe Pro Ser Gly Pro Ala His Phe Thr Cys Asn Ser
                195                 200                 205
Trp Val Gln Pro Thr Arg Val Asp Arg Asn Pro Arg Val Phe Phe Thr
                210                 215                 220
Asn Lys Pro Tyr Leu Pro Ala Glu Thr Pro Pro Gly Leu Gln Glu Leu
225                 230                 235                 240
Arg Arg Gln Glu Leu Ser Asp Leu Arg Gly Glu Gly Ala Asp Thr
                245                 250                 255
Thr Gly Glu Arg Arg Ile Thr Asp Arg Val Trp Glu Tyr Asp Val Tyr
                260                 265                 270
Asn Asp Leu Gly Asn Pro Asp Lys Gly Ala Glu Phe Ala Arg Pro Ile
                275                 280                 285
Leu Gly Gly Glu Gln Gln Leu Pro Tyr Pro Arg Arg Met Arg Thr Gly
                290                 295                 300
Arg Pro Lys Thr Phe Thr Asp Arg Ala Glu Ser Arg Val Glu Tyr
305                 310                 315                 320
Pro Glu Pro Ile Tyr Val Ser Arg Asp Glu Glu Phe Glu Glu Gly Lys
                325                 330                 335
Asn Glu Met Leu Ser Glu Gly Ala Leu Lys Ala Leu Leu His Asn Phe
                340                 345                 350
Met Pro Leu Leu Val Ser Ser Val Ser Pro Asp Ile Arg Asp Phe Ala
                355                 360                 365
Gly Phe His Asp Val Asp Asn Leu Phe Lys Glu Gly Leu Arg Leu Lys
                370                 375                 380
Gln Ala Leu Gln Asp Gln Leu Phe Gln Lys Ile Pro Phe Val Arg Lys
385                 390                 395                 400
Ile

<210> SEQ ID NO 12
<211> LENGTH: 1206
```

<212> TYPE: DNA
<213> ORGANISM: Sorghum bicolor

<400> SEQUENCE: 12

```
atggcgtcgg cgatggagct ggttgggaga tctttcttgc cgggctctgc cgccgcggcg      60
tcgccggcgg gccgggagcg gcggcgaggc gggccctgct tcgccgcggt cggaagggag     120
gggagtgcgc acaagcggcg gccgtcgctg aggtcgaccg cgccggtggg cgcgctggcc     180
gagcgcgtcg tggtgacccc ggcgccgccg aggagaggg ccgggacggc cccgccggag      240
ccgcacccgc agagcgtggc cgcgcgcgcc gtggtcaccg tgcggcggag cgcaaggag      300
gacgccaagc gccgcgtcgc cgagcagctg acgcctacg ccgacagggt cggccgcagc      360
gtcctcctcg agctcatcag cacggagacc gacccaagaa aaggggggcc caagaagagc     420
cggcggtcgg cgctggtggg gtggttcgag aagaaggacg tcaaggcgga gcgggtggtg    480
tacacggcgg acttcaccgt cgacgggtgc ttcggcgagc ctggcgccgt caccgtgctc    540
aaccggcacc agcgcgagtt cttcatcgag agcatcgtgg tggagggctt ccctcgggc     600
cccgcgcact tcacctgcaa ctcgtgggtg cagcccaccc gcgtggaccg caacccgcgc    660
gtgttcttca ccaacaagcc ctacctgccg gccgagacgc cgccggggct gcaggagctc    720
cgccgccagg agctcagcga cctgagggc gagggcggcg ccgacaccac cggcgagcgc    780
aggatcaccg accgggtgtg ggagtacgac gtgtacaacg acctcggcaa cccggacaag    840
ggcgccgagt cgcgcgcccc gatcctcggc ggcgagcagc agctgccgta cccgcgccgg    900
atgcgaacgg ccggccaa gaccttcaca gacgatcgcg cggagagcag ggtggagtac      960
ccggagccca tctacgtgtc ccgggacgag gagttcgagg agggcaagaa cgagatgctg    1020
tcggagggcg cgctcaaggc gctgctccac aacttcatgc cgctgctggt gagctccgtg    1080
tcgccggaca tccgcgactt cgccggcttc cacgacgtgg acaacctctt caaggagggc    1140
ctccggctga agcaggcact gcaggaccag ctgttccaga gatcccctt cgtgcgcaag     1200
atctag                                                              1206
```

<210> SEQ ID NO 13
<211> LENGTH: 180
<212> TYPE: DNA
<213> ORGANISM: Sorghum bicolor

<400> SEQUENCE: 13

```
ggcttccacg acgtggacaa cctcttcaag gagggcctcc ggctgaagca ggcactgcag      60
gaccagctgt tccagaagat ccccttcgtg cgcaagatct aggagaacag cgagggcctc    120
ctccgctacg acacgcccga catcatcaag agtaagcgac ccccacccat gatccatgga    180
```

<210> SEQ ID NO 14
<211> LENGTH: 180
<212> TYPE: DNA
<213> ORGANISM: Sorghum bicolor

<400> SEQUENCE: 14

```
ggcttccacg acgtggacaa cctcttcaag gagggcctcc ggctgaagca ggcactgcag      60
gaccagctgt tccagaagat ccccttcgtg cgcaagatcc aggagaacag cgagggcctc    120
ctccgctacg acacgcccga catcatcaag agtaagcgac ccccacccat gatccatgga    180
```

<210> SEQ ID NO 15
<211> LENGTH: 180
<212> TYPE: DNA

<213> ORGANISM: Sorghum bicolor

<400> SEQUENCE: 15

| | | | | | |
|---|---|---|---|---|---|
| gattcgatac | gataagatac | ggggcacgac | aatggtgtgc | tcatgctgtc | attctgtgtg | 60 |
| gcagaggaca | agtttgtgtg | gctgcgcgac | gacgagttcg | cgaggcaggc | gctggctggc | 120 |
| atcaaccccg | tcaacatcga | gcggcttcag | gtacacattt | caatcacaag | cccaacacgc | 180 |

<210> SEQ ID NO 16
<211> LENGTH: 180
<212> TYPE: DNA
<213> ORGANISM: Sorghum bicolor

<400> SEQUENCE: 16

| | | | | | |
|---|---|---|---|---|---|
| gattcgatac | gataagatac | ggggcacgac | aatggtgtgc | tcatgctgtc | attctgtgtg | 60 |
| gcagaggaca | agtttgcgtg | gctgcgcgac | gacgagttcg | cgaggcaggc | gctggctggc | 120 |
| atcaaccccg | tcaacatcga | gcggcttcag | gtacacattt | caatcacaag | cccaacacgc | 180 |

<210> SEQ ID NO 17
<211> LENGTH: 4048
<212> TYPE: DNA
<213> ORGANISM: Sorghum bicolor

<400> SEQUENCE: 17

| | | | | | |
|---|---|---|---|---|---|
| atggcgtcgg | cgatggagct | ggttgggaga | tctttcttgc | cgggctctgc | cgccgcggcg | 60 |
| tcgccggcgg | gccgggagcg | gcggcgaggc | gggccctgct | tcgccgcggt | cggaagggag | 120 |
| gggagtgcgc | acaagcggcg | gccgtcgctg | aggtcgaccg | cgccggtggg | cgcgctggcc | 180 |
| gagcgcgtcg | tggtgacccc | ggcgccgccg | gaggagaggg | ccgggacggc | cccgccggag | 240 |
| ccgcacccgc | agagcgtggc | cgcgcgcgcc | gtggtcaccg | tgcggcggag | cgcaaggag | 300 |
| gacgccaagc | gccgcgtcgc | cgagcagctg | gacgcctacg | ccgacagggt | cggccgcagc | 360 |
| gtcctcctcg | agctcatcag | cacggagacc | gacccaagta | agaaacattt | cttccgtgat | 420 |
| cccacctcca | ccacccccac | cgccgccgcc | gccgccgcgc | gacggcatgg | aattccatgg | 480 |
| cgcatccggc | gggcggttgc | gttgcatctt | tgaattgtat | gctactagca | gtagcacaat | 540 |
| ttggttccat | tttcttctct | cctcctcgcc | cttttttcca | ttccactcgc | cgctccttca | 600 |
| ccttcatgga | aacccgcgcg | cggcgagaat | attccagctg | gtgcgccttg | acgtctgggg | 660 |
| cctctgtctc | cgagtcatca | tctccaaatg | gaccatcacg | tggagctgtc | tctcttgatt | 720 |
| tgatttctgc | caaaagccgc | cgtctttacc | gtctcctcgg | cgtcgaaacg | gaaatggaac | 780 |
| gaattttact | tacgcctggc | ggcgagcatt | cacctgacga | tcgaaatgaa | ttggtggcag | 840 |
| gaaaagggg | ccccaagaag | agccggcggt | cggcgctggt | ggggtggttc | gagaagaagg | 900 |
| acgtcaaggc | ggagcgggtg | gtgtacacgg | cggacttcac | cgtcgacggg | tgcttcggcg | 960 |
| agcctggcgc | cgtcaccgtg | ctcaaccggc | accagcgcga | gttcttcatc | gagagcatcg | 1020 |
| tggtggaggg | ctttccctcg | ggccccgcgc | acttcacctg | caactcgtgg | gtgcagccca | 1080 |
| cccgcgtgga | ccgcaacccg | cgcgtgttct | tcaccaacaa | gccctacctg | ccggccgaga | 1140 |
| cgccgccggg | gctgcaggag | ctccgccgcc | aggagctcag | cgacctgagg | ggcgagggcg | 1200 |
| gcgccgacac | caccggcgag | cgcaggatca | ccgaccgggt | gtgggagtac | gacgtgtaca | 1260 |
| acgacctcgg | caaccggac | aagggcgccg | agttcgcgcg | cccgatcctc | ggcggcgagc | 1320 |
| agcagctgcc | gtacccgcgc | cggatgcgaa | cgggccggcc | caagaccttc | acaggtgcag | 1380 |
| cctccctctc | cgcttttcaat | tcccctctca | ctcttcactt | cttgtcacca | ccgccgtccg | 1440 |

```
ccccataaat cccgcgacag taactgtggc cgaccggaca cggcggaggt cgccgtcgcg    1500
cgtagctttc gtatcgaaac cacccgatcg cgggcgacgt tgaccgaccg acgctaacat    1560
ttcgtcacgc acgcacggtg cttgctgctt tgcttgctcg ctcgcagacg atcgcgcgga    1620
gagcagggtg gagtacccgg agcccatcta cgtgtcccgg gacagggagt tcgaggaggg    1680
caagaacgag atgctgtcgg agggcgcgct caaggcgctg ctccacaact tcatgccgct    1740
gctggtgagc tccgtgtcgc cggacatccg cgacttcgcc ggcttccacg acgtggacaa    1800
cctcttcaag gagggcctcc ggctgaagca ggcactgcag gaccagctgt tccagaagat    1860
ccccttcgtg cgcaagatcc aggagaacag cgagggcctc ctccgctacg acacgcccga    1920
catcatcaag agtaagcgac ccccacccat gatccatgga gattcgatac gataagatac    1980
ggggcacgac aatggtgtgc tcatgctgtc attctgtgtg gcagaggaca agtttgcgtg    2040
gctgcgcgac gacgagttcg cgaggcaggc gctggctggc atcaaccccg tcaacatcga    2100
gcggcttcag gtacacattt caatcacaag cccaacacgc cgcggacatt gagactacac    2160
gtccactgct cgctcatctc actgccgttc gtttcctcgt gtctctcttc caagcgttc     2220 ccgccgatga gcaagctgga cccggccgtg tacggcccgc cggagtcggc catcacggag    2280
gagcacatca tcgggcagct ggacggcatg tcggtgcggc aggcgctgca ggacaaccgg    2340
ctgtacatgc tggactacca cgacatcttc ctgccgttcc tggaccggat caacgcgcag    2400
gacgggcgga aggcctacgg cacgcgcacg ctcttcttcc tgacggcggc gggcacgctc    2460
aagcccatcg ccatcgagct gtgcctgccg cccatgaccg acgggtgcgc gcgcgccaag    2520
cgggtgttca cgccgcccgc cgacgccacc agcaactggc tgtggcagct cgccaaggcg    2580
cacgtctgct ccaacgacgc cggcgtccac cagctcatca accactggta cgacacgaca    2640
ctgtctgtgt cagtcttgca ggaggaggca atctcaaagt caaaagtgtt ggattccact    2700
gatcatgagt tgtgccaggc tgaggacgca cgcgtgcatg gagccgttca tcatctcggc    2760
gcaccggcag ctgagcgcga tgcacccat cttcaagctg ctcaagccgc acatgcgcta     2820
cacgctcaag atcaacgcgc tggcgcggca gatcctcatc aacggcgacg gcgtcatcga    2880
gtccggcttc acccccggcc gctactgcat ggagatgagc tcgttcgcgt accaggagct    2940
ctggcggctc gaccaggagg gcctccctgc cgatctcatc agaaggtaca cagatcaatc    3000
aatcacatga aagttgtgat gcttcgtgcg atgcaatggt gcttgctgac atgggtgttt    3060
tctttgtcac aacacagagg aatggccgtg gaggacccga cgcagccgca cggtctccgg    3120
ctgctgatcg aggactaccc gtacgccacc gacgggctgc tcctctggga cgccatcacg    3180
cggtggtgcg acgcgtacgt ggccatgtac tacccgtccg accaagccgt gcagggcgac    3240
acggagctgc agtcgtggta cagggaggcg gtgcagacgg ggcacgcgga caagcgcggc    3300
gcgccgtggt ggccgcgcct gtcgacgccg ggcgacctgg cgtcgctgct caccacgctg    3360
ctgtggctca cctcggcgca gcacgcggcg ctcaacttcg ggcagtaccc gctgggcggc    3420
tacatcccga accgaccgcc gctcatgcgg cggctggtgc ccgccgacgg cgacccggag    3480
tacgcgcacc tggtggccga cccgcaccgc ttcttcctgt cggcgctgcc cagcctgacg    3540
cagacgacca ccttcatgac cgtcatcgac acgctgtcca cgcactccgc cgacgagcag    3600
tacctcgggg agcggcccga cgaggcgtgg acggccgacc cggcggcgct ggcggcggcg    3660
cgcgagttcg cggacgaggt gcgccgcgcc gaggaggaga tcgaccggcg caacgcggac    3720
acgggacgcc gcaaccggtg cggcgccggc gtgctgccgt acgagctcat ggcgcccacg    3780
```

```
tccgggccgg gcatcacctg ccgcggcatc cccaacagcg tcaccattta gtctctcgcg   3840
gtaccgatag ccatgggaga atctaagca gaagcaaaat gatttttttt ttgctttact    3900
tctcccccat tgccaaattg ccattgattt ggaggtctga acaggtggag tttgatttt   3960 gactagggga gagacactga ggaactgaat gggtgtaaat aatttgttat tatagaaaaa   4020
aaatcaatga aatataatca ttagagtt                                      4048
```

<210> SEQ ID NO 18
<211> LENGTH: 446
<212> TYPE: PRT
<213> ORGANISM: Sorghum bicolor

<400> SEQUENCE: 18

```
Met Ala Ser Ala Met Glu Leu Val Gly Arg Ser Phe Leu Pro Gly Ser
1               5                   10                  15

Ala Ala Ala Ala Ser Pro Ala Gly Arg Glu Arg Arg Gly Gly Pro
            20                  25                  30

Cys Phe Ala Ala Val Gly Arg Glu Gly Ser Ala His Lys Arg Arg Pro
        35                  40                  45

Ser Leu Arg Ser Thr Ala Pro Val Gly Ala Leu Ala Glu Arg Val Val
    50                  55                  60

Val Thr Pro Ala Pro Pro Glu Glu Arg Ala Gly Thr Ala Pro Pro Glu
65                  70                  75                  80

Pro His Pro Gln Ser Val Ala Ala Arg Ala Val Thr Val Arg Arg
                85                  90                  95

Arg Arg Lys Glu Asp Ala Lys Arg Arg Val Ala Glu Gln Leu Asp Ala
            100                 105                 110

Tyr Ala Asp Arg Val Gly Arg Ser Val Leu Leu Glu Leu Ile Ser Thr
        115                 120                 125

Glu Thr Asp Pro Arg Lys Gly Gly Pro Lys Lys Ser Arg Arg Ser Ala
    130                 135                 140

Leu Val Gly Trp Phe Glu Lys Lys Asp Val Lys Ala Glu Arg Val Val
145                 150                 155                 160

Tyr Thr Ala Asp Phe Thr Val Asp Gly Cys Phe Gly Glu Pro Gly Ala
                165                 170                 175

Val Thr Val Leu Asn Arg His Gln Arg Glu Phe Phe Ile Glu Ser Ile
            180                 185                 190

Val Val Glu Gly Phe Pro Ser Gly Pro Ala His Phe Thr Cys Asn Ser
        195                 200                 205

Trp Val Gln Pro Thr Arg Val Asp Arg Asn Pro Arg Val Phe Phe Thr
    210                 215                 220

Asn Lys Pro Tyr Leu Pro Ala Glu Thr Pro Pro Gly Leu Gln Glu Leu
225                 230                 235                 240

Arg Arg Gln Glu Leu Ser Asp Leu Arg Gly Glu Gly Ala Asp Thr
                245                 250                 255

Thr Gly Glu Arg Arg Ile Thr Asp Arg Val Trp Glu Tyr Asp Val Tyr
            260                 265                 270

Asn Asp Leu Gly Asn Pro Asp Lys Gly Ala Glu Phe Ala Arg Pro Ile
        275                 280                 285

Leu Gly Gly Glu Gln Gln Leu Pro Tyr Pro Arg Arg Met Arg Thr Gly
    290                 295                 300

Arg Pro Lys Thr Phe Thr Asp Asp Arg Ala Glu Ser Arg Val Glu Tyr
305                 310                 315                 320

Pro Glu Pro Ile Tyr Val Ser Arg Asp Glu Glu Phe Glu Glu Gly Lys
```

```
                    325                 330                 335
Asn Glu Met Leu Ser Glu Gly Ala Leu Lys Ala Leu Leu His Asn Phe
                340                 345                 350

Met Pro Leu Leu Val Ser Ser Val Ser Pro Asp Ile Arg Asp Phe Ala
            355                 360                 365

Gly Phe His Asp Val Asp Asn Leu Phe Lys Glu Gly Leu Arg Leu Lys
        370                 375                 380

Gln Ala Leu Gln Asp Gln Leu Phe Gln Lys Ile Pro Phe Val Arg Lys
385                 390                 395                 400

Ile Gln Glu Asn Ser Glu Gly Leu Leu Arg Tyr Asp Thr Pro Asp Ile
                405                 410                 415

Ile Lys Lys Asp Lys Phe Ala Trp Leu Arg Asp Asp Glu Phe Ala Arg
            420                 425                 430

Gln Ala Leu Ala Gly Ile Asn Pro Val Asn Ile Glu Arg Leu
        435                 440                 445

<210> SEQ ID NO 19
<211> LENGTH: 18
<212> TYPE: DNA
<213> ORGANISM: Sorghum bicolor

<400> SEQUENCE: 19
gccctcgctg ttctccta                                                18

<210> SEQ ID NO 20
<211> LENGTH: 18
<212> TYPE: DNA
<213> ORGANISM: Sorghum bicolor

<400> SEQUENCE: 20
gccctcgctg ttctcctg                                                18

<210> SEQ ID NO 21
<211> LENGTH: 25
<212> TYPE: DNA
<213> ORGANISM: Sorghum bicolor

<400> SEQUENCE: 21
ccagctgttc cagaagatcc gatcc                                        25

<210> SEQ ID NO 22
<211> LENGTH: 19
<212> TYPE: DNA
<213> ORGANISM: Sorghum bicolor

<400> SEQUENCE: 22
tggcagagga caagtttgc                                               19

<210> SEQ ID NO 23
<211> LENGTH: 18
<212> TYPE: DNA
<213> ORGANISM: Sorghum bicolor

<400> SEQUENCE: 23
ggcagaggac aagtttgt                                                18

<210> SEQ ID NO 24
<211> LENGTH: 19
<212> TYPE: DNA
<213> ORGANISM: Sorghum bicolor
```

```
<400> SEQUENCE: 24
gatgttgacg gggttgatg                                                    19

<210> SEQ ID NO 25
<211> LENGTH: 20
<212> TYPE: DNA
<213> ORGANISM: Sorghum bicolor

<400> SEQUENCE: 25
cctcgtgtct ctcttcccag                                                   20

<210> SEQ ID NO 26
<211> LENGTH: 20
<212> TYPE: DNA
<213> ORGANISM: Sorghum bicolor

<400> SEQUENCE: 26
cctcgtgtct ctcttcccaa                                                   20

<210> SEQ ID NO 27
<211> LENGTH: 20
<212> TYPE: DNA
<213> ORGANISM: Sorghum bicolor

<400> SEQUENCE: 27
atgatgtgct cctccgtgat                                                   20
```